US009422308B2

(12) United States Patent
Kim et al.

(10) Patent No.: US 9,422,308 B2
(45) Date of Patent: Aug. 23, 2016

(54) DERIVATIVES OF DOCOSAHEXAENOYLETHANOLAMIDE AND USES THEREOF

(71) Applicant: The United States of America, as represented by the Secretary, Department of Health and Human Services, Washington, DC (US)

(72) Inventors: Hee-Yong Kim, Potomac, MD (US); Juan Jose Marugan, Gaithersburg, MD (US); Erika E. Englund, Washington, DC (US); Samarjit Patnaik, Gaithersburg, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/387,410

(22) PCT Filed: Mar. 15, 2013

(86) PCT No.: PCT/US2013/032333
§ 371 (c)(1),
(2) Date: Sep. 23, 2014

(87) PCT Pub. No.: WO2013/158302
PCT Pub. Date: Oct. 24, 2013

(65) Prior Publication Data
US 2015/0031878 A1  Jan. 29, 2015

Related U.S. Application Data

(60) Provisional application No. 61/624,741, filed on Apr. 16, 2012.

(51) Int. Cl.
| C07D 495/04 | (2006.01) |
| C07D 213/40 | (2006.01) |
| C07D 319/20 | (2006.01) |
| C07D 205/04 | (2006.01) |
| C07C 235/28 | (2006.01) |
| C07D 309/04 | (2006.01) |
| C07D 333/20 | (2006.01) |
| C07D 235/14 | (2006.01) |
| C07C 233/09 | (2006.01) |
| C07C 233/13 | (2006.01) |
| C07C 233/20 | (2006.01) |
| C07C 233/23 | (2006.01) |
| C07C 233/31 | (2006.01) |
| C07C 233/38 | (2006.01) |
| C07C 233/49 | (2006.01) |
| C07C 255/29 | (2006.01) |
| C07D 295/13 | (2006.01) |
| C07D 295/135 | (2006.01) |
| C07D 295/185 | (2006.01) |
| C07D 307/52 | (2006.01) |

(52) U.S. Cl.
CPC ............ *C07D 495/04* (2013.01); *C07C 233/09* (2013.01); *C07C 233/13* (2013.01); *C07C 233/20* (2013.01); *C07C 233/23* (2013.01); *C07C 233/31* (2013.01); *C07C 233/38* (2013.01); *C07C 233/49* (2013.01); *C07C 235/28* (2013.01); *C07C 255/29* (2013.01); *C07D 205/04* (2013.01); *C07D 213/40* (2013.01); *C07D 235/14* (2013.01); *C07D 295/13* (2013.01); *C07D 295/135* (2013.01); *C07D 295/185* (2013.01); *C07D 307/52* (2013.01); *C07D 309/04* (2013.01); *C07D 319/20* (2013.01); *C07D 333/20* (2013.01); *C07C 2101/04* (2013.01); *C07C 2101/14* (2013.01)

(58) Field of Classification Search
CPC .. C07D 495/04; C07D 213/40; C07D 333/20; C07D 295/13; C07D 295/135; C07D 295/185; C07D 235/14; C07D 307/52; C07D 319/20; C07D 205/04; C07D 309/04; C07C 235/28; C07C 233/31; C07C 233/49; C07C 233/09; C07C 233/20; C07C 233/23; C07C 233/38; C07C 233/13; C07C 255/29; C07C 2101/14; C07C 2101/04
See application file for complete search history.

(56) References Cited

U.S. PATENT DOCUMENTS 9,150,504 B2 * 10/2015 Milne ................ C07C 279/14
2011/0212958 A1    9/2011 Milne et al.

FOREIGN PATENT DOCUMENTS

| EP | 1 852 499 A1 | 11/2007 |
| JP | 08143454 | 11/1994 |
| WO | WO 03/004484 A1 | 1/2003 |
| WO | WO 2012/115695 * | 8/2012 |
| WO | WO 2012/149352 A1 | 11/2012 |

OTHER PUBLICATIONS

Chemical Abstracts Registry No. 485822-61-5, indexed in the Registry file on STN CAS Online on Feb. 5, 2003.*
Bligh et al., "A rapid method of total lipid extraction and purification," *Can. J. Biochem. Physiol.*, 37 (8), 911-917 (1959).
Brown et al., "Cannabinoid receptor-dependent and -independent anti-proliferative effects of omega-3 ethanolamides in androgen receptor-positive and -negative prostate cancer cell lines," *Carcinogenesis*, 31 (9), 1584-1591 (2010) (published online Jul. 25, 2010).
Calderon et al., "Docosahexaenoic acid promotes neurite growth in hippocampal neurons," *J. Neurochem.*, 90 (4), 979-988 (2004), errata in *J. Neurochem.*, Sep; 90 (6); 1540 (2004) (published online Jul. 13, 2004).
Cao et al., "Docosahexaenoic acid promotes hippocampal neuronal development and synaptic function," *J. Neurochem.*, 111, 510-521 (2009) (published online Aug. 13, 2009).

(Continued)

*Primary Examiner* — Shailendra Kumar
(74) *Attorney, Agent, or Firm* — Leydig, Voit & Mayer, Ltd.

(57) ABSTRACT

The invention provides derivatives of DEA which have increased potency and hydrolysis resistance as compared to DEA, and compositions thereof, as well as methods of using these derivatives to promote neurogenesis, neurite growth and/or length, and/or promote synaptogenesis.

22 Claims, 9 Drawing Sheets

(56) References Cited

OTHER PUBLICATIONS

Dang et al., "Evaluation of endogenous fatty acid amides and their synthetic analogues as potential anti-inflammatory leads," *Bioorganic & Medicinal Chemistry*, 19 (4), 1520-1527 (2011) (published online Dec. 30, 2010).

Hayes et al., "Identification of N-acylethanolamines in *Dictyostelium discoideum* and confirmation of their hydrolysis by fatty acid amide hydrolase," *J. Lipid. Res.*, 54 (2), 457-466 (2013), with supplementary data (published online Nov. 27, 2012).

International Search Report, Application No. PCT/US2013/032333, dated May 22, 2013.

Kim et al., "A synaptogenic amide N-docosahexaenoylethanolamide promotes hippocampal development," *Prostaglandins & Other Lipid Mediat.*, 96 (1-4), 114-120 (2011), author manuscript (published online Jul. 23, 2011).

Kim et al., "N-Docosahexaenoylethanolamide promotes development of hippocampal neurons," *Biochem. J.*, 435 (2), 327-336 (2011), incorrectly cited in the ISR as *Biochem. J.*, 83 (2), 1017-1336 (2011) (author manuscript).

Kono et al., "Synthesis, SAR study, and biological evaluation of a series of piperazine ureas as fatty acid amide hydrolase (FAAH) inhibitors," *Bioorganic & Medicinal Chem.*, 21 (1), 28-41 (2013) (published online Nov. 15, 2012).

MacCarrone et al., "A sensitive and speCific radiochromatographic assay of fatty acid amide hydrolase activity," *Analytical Biochem.*, 267 (2), 314-318 (1999).

Written Opinion of the International Searching Authority, Application No. PCT/US2013/032333, dated Oct. 16, 2014.

Yamamoto et al., Identification of putative metabolites of docosahexaenoic acid as potent PPAR$\gamma$ agonists and antidiabetic agents, *Bioorg. Med. Chem. Lett.*, 15 (3), 517-522 (2005) (published online Dec. 16, 2004).

Yang et al., "Decoding Functional Metabolomics with Docosahexaenoyl Ethanolamide (DHEA) Identifies Novel Bioactive Signals," *J. Biol. Chem.*, 286 (36), 31532-31541 (2011) (published online Jul. 12, 2011).

* cited by examiner

US 9,422,308 B2

DERIVATIVES OF DOCOSAHEXAENOYLETHANOLAMIDE AND USES THEREOF

CROSS-REFERENCE TO RELATED APPLICATION

This patent application is a U.S. National Phase of International Patent Application No. PCT/US2013/032333, filed Mar. 15, 2013, which claims the benefit of U.S. Provisional Patent Application No. 61/624,741, filed Apr. 16, 2012, each of which is incorporated by reference in its entirety.

BACKGROUND OF THE INVENTION

Docosahexanenoic acid (DHA) is an n-3 essential fatty acid that is highly enriched in the brain, and which increases neurogenesis, neurite growth, and synaptogenesis. Docosahexaenoylethanolamide (DEA, also called "synaptamide") is a DHA derivative that also has been shown to increase hippocampal development and synaptic function. Agents capable of neurogenesis, neurite growth, and synaptogenesis are desirable for use in treating central nervous system (CNS) conditions, especially conditions such as stroke, neurodegenerative diseases, and brain injuries.

Additional DHA derivatives are needed which have increased potency and stability.

BRIEF SUMMARY OF THE INVENTION

In an aspect, the invention provides derivatives of synaptamide which have increased potency and hydrolysis resistance as compared to synaptamide, and compositions thereof.

In another aspect, the invention provides a method of promoting neurite growth and/or length, and/or promoting synaptogenesis, comprising applying to a neuron a compound having the formula $CH_3CH_2HC=CHCH_2HC=CHCH_2HC=CHCH_2HC=CHCH_2HC=CHCH_2HC=CHCH_2HC=CHCH_2CH_2CO-NR^1R^2$, wherein the group $NR^1R^2$ is as provided in Table 1 below, and measuring the growth and/or length of a neurite of the neuron, wherein neurite growth and/or length is promoted if the length/growth of the neurite is greater than the length/growth of a control neurite of an untreated neuron and synaptogenesis is promoted if the number and/or percent increase of synapsin-positive puncta is greater than that of untreated control.

In yet another aspect, the invention provides a method of promoting neurogenesis, comprising applying to a tissue comprising neural stem cells a compound having the formula $CH_3CH_2HC=CHCH_2HC=CHCH_2HC=CHCH_2HC=CHCH_2HC=CHCH_2HC=CHCH_2CH_2CO-NR^1R^2$, wherein the group $NR^1R^2$ is as provided in Table 1 below, and measuring the differentiation of neurons in the tissue, wherein neurogenesis is promoted if the number and/or percent increase of neurons in a treated sample of the tissue or stein cells is increased as compared to an untreated control sample.

DETAILED DESCRIPTION OF THE INVENTION

Figure 1:
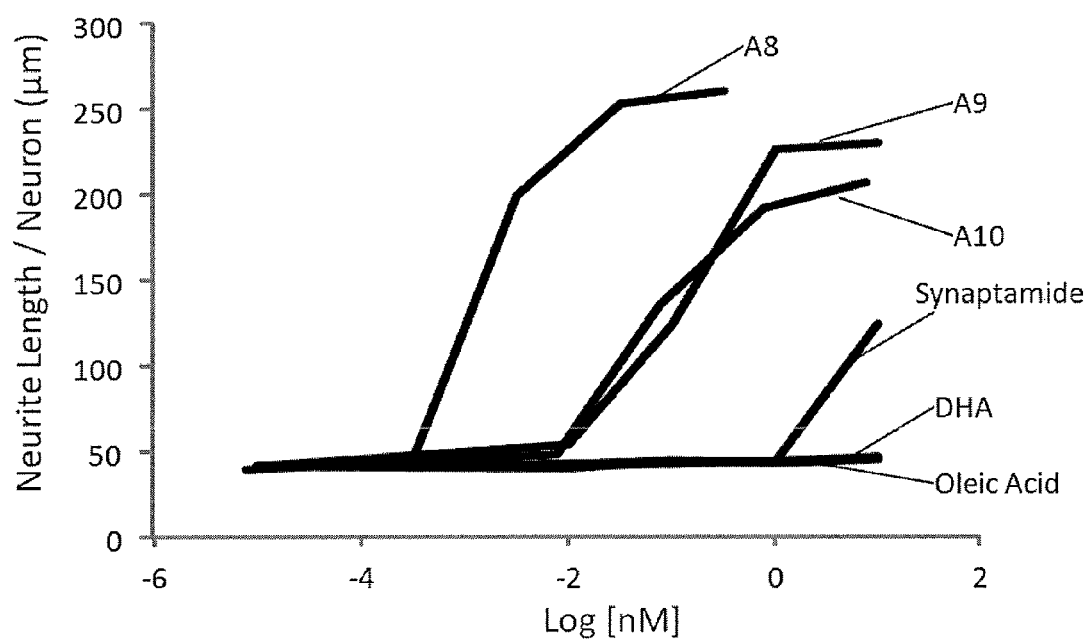
FIG. 1 is a plot of neurite length by dosage for three synaptamide derivatives (A8, A9, and A10) as compared to DHA, DEA (synaptamide), and oleic acid, in accordance with embodiments of the invention.

The present invention relates to synaptamide derivatives and compositions thereof, which can be used to increase neurogenesis, neurite growth and/or length, synaptogenesis, and/or synaptic protein expression. Contemplated synaptamide derivatives have the formula:

$CH_3CH_2HC=CHCH_2HC=CHCH_2HC=CHCH_2HC=CHCH_2HC=CHCH_2HC=CHCH_2CH_2CO-NR^1R^2$, wherein the group $NR^1R^2$ is as provided in Table 1 below. It is surprisingly shown herein that synaptamide derivatives of the present invention have increased potency as compared to synaptamide and improved resistance to hydrolysis by fatty acid amide hydrolase (FAAH).

TABLE 1

| Compound | NR¹R² | Compound identifier in FIGS. 1-4 | NCGC* |
|---|---|---|---|
| 1 | (N-H)-CH₂-C(CH₃)₂-OH | A8 (FIGS. 1, 2, 4-7) | NCGC00248435-01 |
| 2 | (N-H)-(CH₂)₄-OH | A7 (FIGS. 2, 4) | NCGC00248434-01 |
| 3 | (N-H)-(CH₂)₃-OH | A4 (FIGS. 2, 4) | NCGC00248431-01 |
| 4 | (N-H)-CH₂CH₂-morpholine | A10 (FIGS. 1, 2, 4) | NCGC00248437-01 |
| 5 | (N-H)-CH₂CH₂-N(CH₃)₂ | A5 (FIGS. 2, 4) | NCGC00248432-01 |
| 6 | (N-H)-CH₂CH₂-OCH₃ | A1 (FIGS. 2, 4) | NCGC00248428 |
| 7 | (N-H)-CH₂CH₂-Ph | A9 (FIGS. 1, 2, 4) | NCGC00248436-01 |
| 8 | (N-H)-C(CH₃)₂-CH₂OH | A6 (FIGS. 2, 4) | NCGC00248433-01 |
| 9 | (N-H)-CH(CH₃)-CH₂OH (S) | A2 (FIGS. 2, 4) | NCGC00248429-01 |
| 10 | (N-H)-CH(CH₃)-CH₂OH (R) | A3 (FIGS. 2, 4) | NCGC00248430-01 |
| 11 | (N-H)-CH₂-(2,3-dihydro-1,4-benzodioxin-2-yl) | A01 (FIG. 3) | NCGC00250349-01 |

TABLE 1-continued

| Compound | NR¹R² | Compound identifier in FIGS. 1-4 | NCGC* |
|---|---|---|---|
| 12 | | B01 (FIG. 3) | NCGC00250369-01 |
| 13 | | C01 (FIG. 3) | NCGC00250337-01 |
| 14 | | D01 (FIG. 3) | NCGC00250347-01 |
| 15 | | E01 (FIG. 3) | NCGC00250365-01 |
| 16 | | F01 (FIG. 3) | NCGC00250370-01 |
| 17 | | G01 (FIG. 3) | NCGC00250371-01 |
| 18 | | H01 (FIG. 3) | NCGC00250367-01 |
| 19 | | A02 (FIG. 3) | NCGC00250340-01 |
| 20 | | B02 (FIG. 3) | NCGC00250351-01 |
| 21 | | C02 (FIG. 3) | NCGC00250348-01 |

TABLE 1-continued
| Compound | NR¹R² | Compound identifier in FIGS. 1-4 | NCGC* |
|---|---|---|---|
| 22 | 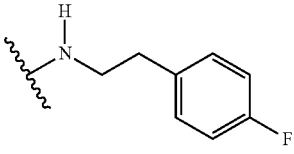 [SMILES: *NCCc1ccc(F)cc1] | D02 (FIG. 3) | NCGC00250357-01 |
| 23 | 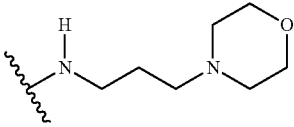 [SMILES: *NCCCN1CCOCC1] | E02 (FIG. 3) | NCGC00250334-01 |
| 24 | 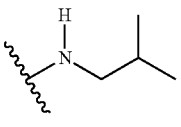 [SMILES: *NCC(C)C] | F02 (FIG. 3) | NCGC00250342-01 |
| 25 | 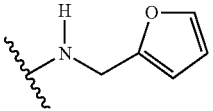 [SMILES: *NCc1ccco1] | G02 (FIG. 3) | NCGC00250354-01 |
| 26 | 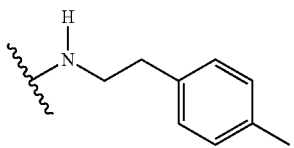 [SMILES: *NCCc1ccc(C)cc1] | H02 (FIG. 3) | NCGC00250355-01 |
| 27 | 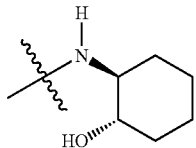 [SMILES: *N[C@H]1CCCC[C@@H]1O] | A03 (FIG. 3) | NCGC00250343-01 |
| 28 | 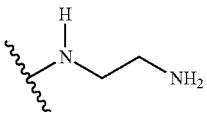 [SMILES: *NCCN] | B03 (FIG. 3) | NCGC00250333-01 |
| 29 | 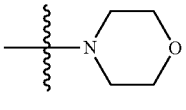 | C03 (FIG. 3) | NCGC00250339-01 |
| 30 | 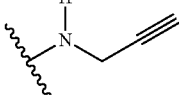 | D03 (FIG. 3) | NCGC00250362-01 |
| 31 | 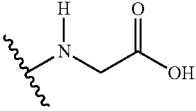 [SMILES: *NCC(=O)O] | E03 (FIG. 3) | NCGC00161207-03 |
| 32 | 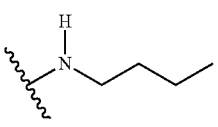 [SMILES: *NCCCC] | F03 (FIG. 3) | NCGC00250363-01 |

TABLE 1-continued

| Compound | NR¹R² | Compound identifier in FIGS. 1-4 | NCGC* |
|---|---|---|---|
| 33 | (1-phenyl-2,2,2-trifluoroethyl)amino | G03 (FIG. 3) | NCGC00250358-01 |
| 34 | 2-(pyridin-3-yl)ethylamino | H03 (FIG. 3) | NCGC00250346-01 |
| 35 | 2-(2-chlorophenyl)ethylamino | A04 (FIG. 3) | NCGC00250359-01 |
| 36 | (3-(dimethylamino)-2,2-dimethylpropyl)amino | B04 (FIG. 3) | NCGC00250366-01 |
| 37 | 2-(2,4-dichlorophenyl)ethylamino | C04 (FIG. 3) | NCGC00250356-01 |
| 38 | (2-oxo-2-phenylethyl)amino | D04 (FIG. 3) | NCGC00250345-01 |
| 39 | (2,3-dihydrobenzo[b][1,4]dioxin-6-yl)amino | E04 (FIG. 3) | NCGC00250353-01 |
| 40 | (2-(diisopropylamino)ethyl)amino | F04 (FIG. 3) | NCGC00250364-01 |
| 41 | (2-(pyrrolidin-1-yl)ethyl)amino | G04 (FIG. 3) | NCGC00250336-01 |
| 42 | (2-hydroxy-2-phenylethyl)amino | H04 (FIG. 3) | NCGC00250344-01 |

TABLE 1-continued

| Compound | NR¹R² | Compound identifier in FIGS. 1-4 | NCGC* |
|---|---|---|---|
| 43 | 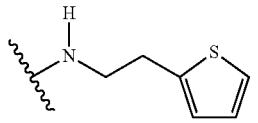 [SMILES: *NCCc1cccs1] | A05 (FIG. 3) | NCGC00250352-01 |
| 44 | 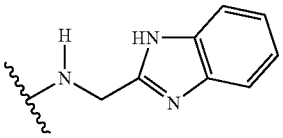 [SMILES: *NCc1nc2ccccc2[nH]1] | B05 (FIG. 3) | NCGC00250360-01 |
| 45 | 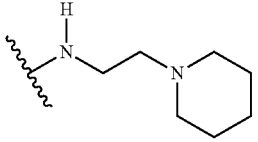 [SMILES: *NCCN1CCCCC1] | C05 (FIG. 3) | NCGC00250335-01 |
| 46 | 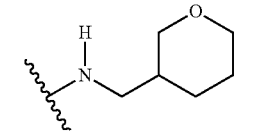 [SMILES: *NCC1CCCOC1] | D05 (FIG. 3) | NCGC00250338-01 |
| 47 | 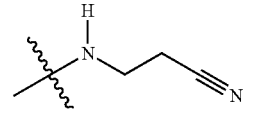 [SMILES: *NCCC#N] | E05 (FIG. 3) | NCGC00250368-01 |
| 48 | 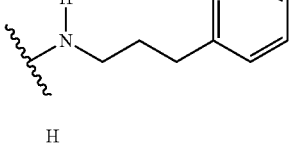 | F05 (FIG. 3) | NCGC00250361-01 |
| 49 | 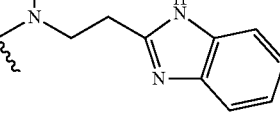 | G05 (FIG. 3) | NCGC00250341-01 |
| 50 | 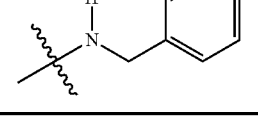 | H05 (FIG. 3) | NCGC00250350-01 |

* "-01" designates batch.

The present invention also provides methods of using the disclosed synaptamide derivatives and compositions thereof. In some embodiments, the invention provides a method of promoting cortical and/or hippocampal development, which can be reflected by, for example, promotion of neurite growth and/or length, and/or promotion of synaptogenesis. In other embodiments, the invention provides a method of promoting neurogenesis, i.e., enhancement of neuronal differentiation of neural stem cells.

In another aspect, the invention provides a method of promoting neurite growth and/or length, and/or promoting synaptogenesis, comprising applying to a neuron a compound of the present invention, and measuring the growth and/or length of a neurite of the neuron, wherein neurite growth and/or length is promoted if the length/growth of the neurite is greater than the length/growth of a control neurite of an untreated neuron, and synaptogenesis is promoted if the number and/or percent increase of synapsin-positive puncta is greater than that of untreated control. Alternatively, synaptogenesis can be measured by evaluating expression of synaptic proteins such as synapsin, PSD95 and/or NMDA receptor subunits such as NR2B.

It will be understood that any suitable method of measuring neurite growth and/or length and/or measuring synaptogenesis can be employed in the methods of the present invention.

In particular, methods employed for measuring the activity of synaptamide itself are suitable and desirable for measurement of the present synaptamide derivatives. Exemplary methods of evaluating synaptamide activity can be found in Kim et al., *Biochem J.*, 435: 327-336 (2011); Cao et al., *J. Neurochem.*, 111: 510-521 (2009); and Kim et al., *Prostaglandins & Other Lipid Mediators*, 96(1-4):114-120 (2011), each of which are incorporated by reference for the described methods. In preferred embodiments, the neuron is in a subject, i.e., the treatment is applied in vivo. In other embodiments, the neuron is in a culture, i.e., the treatment is applied in vitro. When a subject has been treated in vivo, analysis of the neurite growth and/or length and/or analysis of the synaptogenesis can be performed on a sample that has been removed from a treated subject, i.e., ex vivo.

In a related aspect, the invention provides a method of promoting neurogenesis, comprising applying a synaptamide derivative of the present invention to a tissue comprising neural stem cells, wherein neurogenesis is promoted if the number and/or percent increase of neurons in a treated sample of the tissue is increased as compared to an untreated control sample. The number/percent increase of neurons can be measured by any suitable method known to one of ordinary skill in the art by direct or indirect methods. For example, the number of neurons can be observed directly via microscopy of a sample of treated tissue. Direct, microscopic observation is preferred when the tissue is in a culture, or when the tissue is in a non-human subject. However, if the tissue is in a human subject, indirect methods such as behavioral test (motor function and/or learning and memory test) are preferably applied to determine whether neurogenesis has occurred.

The methods of the present invention can be conducted in any suitable subject. In preferred embodiments, the subject is a mammal, such as a mouse, rat, rabbit, cat, dog, pig, cow, horse, non-human primate or human. In most preferred embodiments, the subject is a human. It will be understood by one of ordinary skill in the art that controls in the methods of the present invention are preferably from the same species as the subject.

In the methods of the present invention, the subject suffers from a CNS condition. Preferably, the CNS condition is a neurological condition. The condition can be an injury, such as a stroke, traumatic brain injury, spinal cord injury, or peripheral nerve injury. Alternatively, the condition can be a neurodegenerative disease such as multiple sclerosis, Huntington's disease, Parkinson's disease, amyotrophic lateral sclerosis, Alzheimer's disease, or other types of dementia. In some embodiments, the neurological condition is a condition such as autism. In preferred embodiments, controls in the methods of the present invention preferably have the same CNS condition as the subject.

It will be understood by one of ordinary skill in the art that a method can be deemed to promote a desired activity, such as neurogenesis, neurite growth/length, and/or synaptogenesis, if the method results in an increase of such activity over an untreated or sham-treated control. It is not necessarily required that levels be restored to normal or to be enhanced above normal by any particular amount or percentage, unless such amount or percentage is otherwise specified. To the extent the compounds of the present invention are administered to an individual suffering from a CNS condition as described above in order to treat or prevent such condition or symptoms arising therefrom, the terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease or injury being treated or prevented. Also, for purposes herein, "prevention" can encompass delaying the onset of the disease, or a symptom or condition thereof.

As would be appreciated in the art, any comparisons discussed herein, when part of the methods of the present invention, involve the use of proper controls. For example, when the length of a neurite of a first neuron is measured and compared to the length of a neurite of a control neuron, the control neurite should be a neurite that has a starting length that is similar to or the same as the starting length of the neurite of the first neuron. Such a comparison would involve absolute length. Additionally or alternatively, the starting lengths of the neurites may be different and the growth (increase in length of the neurite of the first neuron relative to the increase in length of the neurite of the control neuron) may be compared. The same concept for length/growth applies to the number/percent increase of neurons or synapsin-positive puncta. When the number of neurons or puncta of a test group is measured and compared to the number of neurons or puncta of a control, the control should have a starting number that is similar to or the same as the starting number of the test group. Such a comparison would involve absolute number. Additionally or alternatively, the starting numbers may be different and the percent increase (increase in number of the test group relative to the increase in number of the control) may be compared.

In one embodiment, the present invention provides a method of promoting neurite growth and/or length within a mammal, the method comprising administering to the mammal an effective amount of a compound of Table 1, wherein neurite growth and/or length is promoted in the mammal.

In another embodiment, the present invention provides a method wherein the method further comprises measuring the growth and/or length of a neurite of a neuron of the mammal.

In another embodiment, the present invention provides a method wherein the method further comprises measuring the growth and/or length of a neurite of a control.

In another embodiment, the present invention provides a method wherein the growth of the neurite of the mammal is greater than the growth of the neurite of the control.

In another embodiment, the present invention provides a method wherein the length of the neurite of the mammal is greater than the length of the neurite of the control.

In another embodiment, the present invention provides a method wherein the mammal has a neurological condition selected from traumatic brain injury, spinal cord injury, peripheral nerve injury, stroke, multiple sclerosis, autism, Alzheimer's disease, Huntington's disease, Parkinson's disease, amyotrophic lateral sclerosis.

In another embodiment, the present invention provides a method wherein the control is a neuron of a second mammal.

In another embodiment, the present invention provides a method wherein the mammal has a neurological condition selected from traumatic brain injury, spinal cord injury, peripheral nerve injury, stroke, multiple sclerosis, autism, Alzheimer's disease, Huntington's disease, Parkinson's disease, amyotrophic lateral sclerosis, and wherein the second mammal has the same neurological condition.

In another embodiment, the present invention provides a method wherein the compound is provided in a pharmaceutically acceptable composition.

In another embodiment, the present invention provides a method of promoting neurogenesis within a mammal, the method comprising administering to the mammal an effective amount of a compound of Table 1, wherein neurogenesis is promoted in the mammal.

In another embodiment, the present invention provides a method wherein the method further comprises measuring the number and/or percent increase of neurons or synapsin-positive puncta of a neuron of the mammal.

In another embodiment, the present invention provides a method wherein the method further comprises measuring the number and/or percent increase of neurons or synapsin-positive puncta of a neuron of a control.

In another embodiment, the present invention provides a method wherein the number of neurons of the mammal is greater than the number of neurons of the control.

In another embodiment, the present invention provides a method wherein the percent increase of neurons of the mammal is greater than the percent increase of neurons of the control.

In another embodiment, the present invention provides a method wherein the number of synapsin-positive puncta of the mammal is greater than the number of synapsin-positive puncta of the control.

In another embodiment, the present invention provides a method wherein the percent increase of synapsin-positive puncta of the mammal is greater than the percent increase of synapsin-positive puncta of the control.

In another embodiment, the present invention provides a method wherein the mammal has a neurological condition selected from traumatic brain injury, spinal cord injury, peripheral nerve injury, stroke, multiple sclerosis, autism, Alzheimer's disease, Huntington's disease, Parkinson's disease, amyotrophic lateral sclerosis.

In another embodiment, the present invention provides a method wherein the control comprises a neuron of a second mammal.

In another embodiment, the present invention provides a method wherein the mammal has a neurological condition selected from traumatic brain injury, spinal cord injury, peripheral nerve injury, stroke, multiple sclerosis, autism, Alzheimer's disease, Huntington's disease, Parkinson's disease, amyotrophic lateral sclerosis, and wherein the second mammal has the same neurological condition.

The synaptamide derivatives of the present invention can be provided in a composition, such as a pharmaceutical composition suitable for therapeutic or prophylactic use, or a composition suitable for analytical use. For pharmaceutical compositions, the synaptamide derivatives can be provided in a composition with any pharmaceutically acceptable carrier. Desirably, the composition is formulated to provide suitable levels of CNS penetration in view of the desired route of administration.

The composition can be formulated for administration by a route selected from intravenous, intraarterial, intramuscular, intraperitoneal, intrathecal, epidural, topical, percutaneous, subcutaneous, transmucosal, intranasal, or oral. The composition also can comprise additional components such as diluents, adjuvants, excipients, preservatives, and pH adjusting agents, and the like.

Formulations suitable for injectable administration include aqueous and nonaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, or tablets.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The active ingredients can also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are known in the art, e.g., as disclosed in Remington's Pharmaceutical Sciences 16th edition, Osol, A. Ed. (1980). Specifically, liposomes containing the synaptamide derivatives can be prepared by such methods as described in, for example, Rezler et al., *J. Am. Chem. Soc.* 129(16): 4961-72 (2007); Samad et al., *Curr. Drug Deliv.* 4(4): 297-305 (2007); and U.S. Pat. Nos. 4,485,045 and 4,544,545. Liposomes with enhanced circulation time are disclosed in, for example, U.S. Pat. No. 5,013,556.

Particularly useful liposomes can be generated by, for example, the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Polypeptides of the present invention can be conjugated to the liposomes as described in, for example, Werle et al., *Int. J. Pharm.* 370(1-2): 26-32 (2009).

In other embodiments, the active ingredients can be delivered using a natural virus or virus-like particle, a dendrimer, carbon nanoassembly, a polymer carrier, a paramagnetic particle, a ferromagnetic particle, a polymersome, a filomicelle, a micelle or a lipoprotein.

Administration into the airways can be used to provide systemic administration, for example to the trachea and/or the lungs. Such administration can be made via inhalation or via physical application, using aerosols, solutions, and devices such as a bronchoscope. For inhalation, the compositions herein are conveniently delivered from an insufflator, a nebulizer, a pump, a pressurized pack, or other convenient means of delivering an aerosol, non-aerosol spray of a powder, or non-aerosol spray of a liquid. Pressurized packs can comprise a suitable propellant such a liquefied gas or a compressed gas. Liquefied gases include, for example, fluorinated chlorinated hydrocarbons, hydrochlorofluorocarbons, hydrochlorocarbons, hydrocarbons, and hydrocarbon ethers. Compressed gases include, for example, nitrogen, nitrous oxide, and carbon dioxide. In particular, the use of dichlorodifluoromethane, trichlorofluoromethane, dichlorotetrafluoroethane, carbon dioxide or other suitable gas is contemplated. In the case of a pressurized aerosol, the dosage unit can be determined by providing a valve to deliver a controlled amount. In administering a dry powder composition, the powder mix can include a suitable powder base such as lactose or starch. The powder composition can be presented in unit dosage form such as, for example, capsules, cartridges, or blister packs from which the powder can be administered with the aid of an inhalator or insufflator.

Systemic administration can also be transmucosal. For transmucosal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, inhaled aerosols, suppositories, mouthwashes, rapidly dissolving tablets, or lozenges.

The pharmaceutical compositions can be delivered using drug delivery systems. Such delivery systems include hyaluronic acid solutions or suspensions of collagen fragments. The drugs can be formulated in microcapsules, designed with appropriate polymeric materials for controlled release, such as polylactic acid, ethylhydroxycellulose, polycaprolactone, polycaprolactone diol, polylysine, polyglycolic, polymaleic acid, poly[N-(2-hydroxypropyl)methylacrylamide] and the like. Particular formulations using drug delivery systems can be in the form of liquid suspensions or the like.

The following examples further illustrate the invention but, of course, should not be construed as in any way limiting its scope.

Example 1

This example demonstrates the preparation of derivatives of docosahexaenoylethanolamide.

A solution of (4Z,7Z,10Z,13Z,16Z,19Z)-docosa-4,7,10,13,16,19-hexaenoic acid (150 mg, 0.46 mmol), and diisopropylethylamine (DIPEA) (0.16 mL, 0.91 mmol) in $CH_3CN$ (6 mL) was treated with O-(7-Azabenzotriazol-1-yl)-N,N,N',N'-tetramethyluronium hexafluorophosphate (HATU) (400 mg, 1.05 mmol)) and stirred at room temperature for 5 min. The reaction mixture was treated with amine $NR^1R^2$ (0.55 mmol), stirred at room temperature for 3 h and quenched with $NaHCO_3$ (sat.). The reaction mixture was extracted with EtOAc, dried ($MgSO_4$), filtered, and concentrated under reduced pressure. The product was purified via column chromatography on $SiO_2$ (0-10% $MeOH/CH_2Cl_2$) to afford the desired product.

The resulting derivatives (Compounds 1-50) were analyzed by $^1H$ NMR analysis, high performance liquid chromatography (HPLC) analysis, UV transmission analysis ($UV_{254}$), liquid chromatography-mass spectrometry (LCMS) analysis, and high resolution mass spectrometry (HRMS) analysis. The HPLC retention times $t_R$ reported were obtained using the following specifications: Column: Phenomenex Luna C18 (3 micron, 3×75 mm); Run time: 8 min; Gradient: 4% to 100% Acetonitrile in water over 7 min; Mobile phase: Acetonitrile (0.025% TFA), water (0.05% TFA); Flow rate: 1 mL/min; Temperature: 50° C.; UV wavelength: 220 nm, 254 nm. Some retention times (marked with *) were acquired under similar conditions but with a shorter run time of 5 min with the same gradient over 3 min.

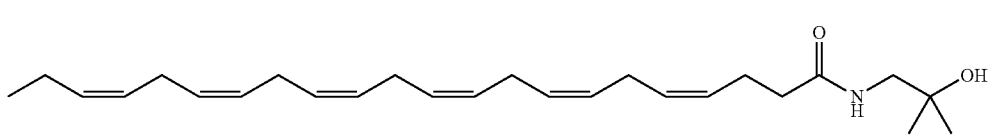

(Compound 1)

Compound 1, having the formula (4Z,7Z,10Z,13Z,16Z,19Z)—N-(2-hydroxy-2-methylpropyl)docosa-4,7,10,13,16,19-hexaenamide exhibited the following properties: $^1H$ NMR (400 MHz, CHLOROFORM-d) δ 5.28-5.47 (m, 12H) 3.27 (d, J=6.26 Hz, 2H) 2.85 (t, J=5.28 Hz, 10H) 2.39-2.48 (m, 3H) 2.29 (t, J=7.24 Hz, 2H) 2.03-2.13 (m, 2H) 1.22 (s, 6H) 0.93-1.01 (m, 3H); HPLC: $t_R$=7.47 min, $UV_{254}$=99%; LCMS: (electrospray +ve), m/z 400.3 $(MH)^+$; HRMS (ESI): m/z calcd for $C_{26}H_{42}NO_2$ $[M+1]^+$ 400.3210. found 400.3221.

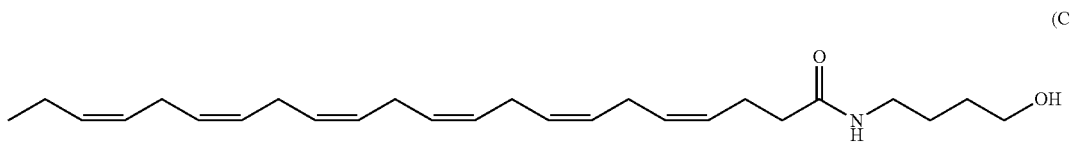

(Compound 2)

Compound 2, having the formula (4Z,7Z,10Z,13Z,16Z,19Z)—N-(4-hydroxybutyl)docosa-4,7,10,13,16,19-hexaenamide exhibited the following properties: HPLC: $t_R$=7.28 min, $UV_{254}$=99%; LCMS: (electrospray +ve), m/z 400.3 (MH)$^+$; HRMS (ESI): m/z calcd for $C_{26}H_{42}NO_2$ [M+1]$^+$ 400.3210. found 400.3220.

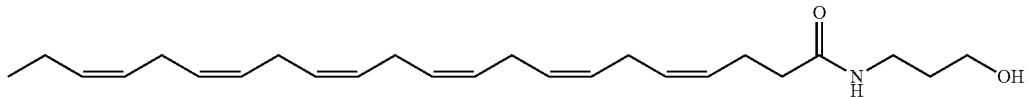

(Compound 3)

Compound 3, having the formula (4Z,7Z,10Z,13Z,16Z,19Z)—N-(3-hydroxypropyl)docosa-4,7,10,13,16,19-hexaenamide exhibited the following properties: HPLC: $t_R$=7.72 min, $UV_{254}$=99%; LCMS: (electrospray +ve), m/z 386.3 (MH)$^+$; HRMS (ESI): m/z calcd for $C_{25}H_{39}NO_2Na$ [M+Na]$^+$ 408.2873. found 408.2876.

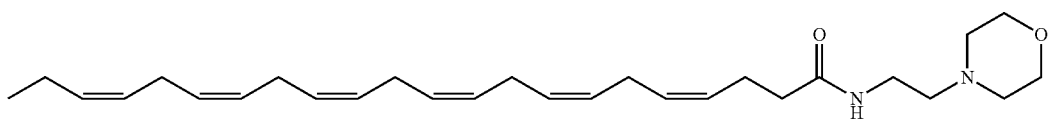

(Compound 4)

Compound 4, having the formula (4Z,7Z,10Z,13Z,16Z,19Z)—N-(2-morpholinoethyl)docosa-4,7,10,13,16,19-hexaenamide exhibited the following properties: HPLC: $t_R$=6.03 min, $UV_{254}$=98%; LCMS: (electrospray +ve), m/z 441.3 (MH)$^+$; HRMS (ESI): m/z calcd for $C_{28}H_{45}N_2O_2$ [M+1]$^+$ 441.3476. found 441.3466.

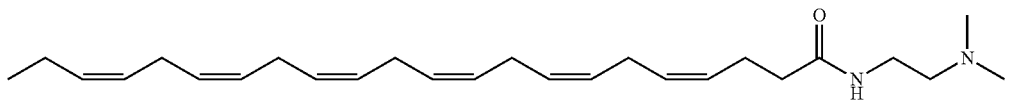

(Compound 5)

Compound 5, having the formula (4Z,7Z,10Z,13Z,16Z,19Z)—N-(2-(dimethylamino)ethyl)docosa-4,7,10,13,16,19-hexaenamide exhibited the following properties: HPLC: $t_R$=6.01 min, $UV_{254}$=98%; LCMS: (electrospray +ve), m/z 399.3 (MH)$^+$; HRMS (ESI): m/z calcd for $C_{26}H_{43}N_2O$ [M+1]$^+$ 399.3370. found 399.3370.

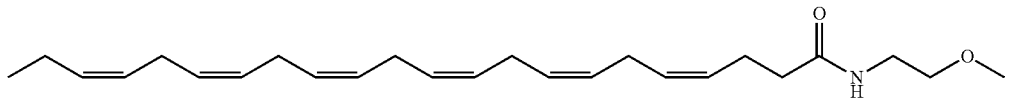

(Compound 6)

Compound 6, having the formula (4Z,7Z,10Z,13Z,16Z,19Z)—N-(2-methoxyethyl)docosa-4,7,10,13,16,19-hexaenamide exhibited the following properties: HPLC: $t_R$=7.58 min, $UV_{254}$=99%; LCMS: (electrospray +ve), m/z 386.2 (MH)$^+$; HRMS (ESI): m/z calcd for $C_{25}H_{40}NO_2$ [M+1]$^+$ 386.3054. found 386.3051.

(Compound 7)

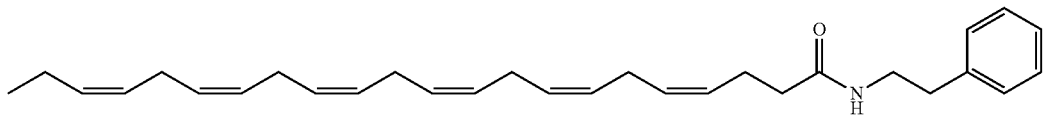

Compound 7, having the formula (4Z,7Z,10Z,13Z,16Z,19Z)—N-phenethyldocosa-4,7,10,13,16,19-hexaenamide exhibited the following properties: HPLC: $t_R$=7.97 min, $UV_{254}$=98%; LCMS: (electrospray +ve), m/z 432.3 (MH)$^+$; HRMS (ESI): m/z calcd for $C_{30}H_{42}NO$ [M+1]$^+$ 432.3261. found 432.3248.

(Compound 8)

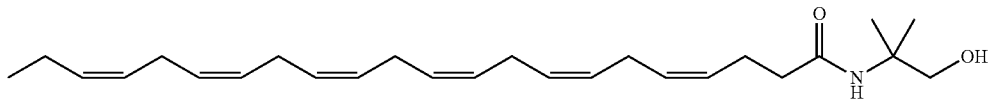

Compound 8, having the formula (4Z,7Z,10Z,13Z,16Z,19Z)—N-(1-hydroxy-2-methylpropan-2-yl)docosa-4,7,10,13,16,19-hexaenamide exhibited the following properties: HPLC: $t_R$=7.58 min, $UV_{254}$=90%; LCMS: (electrospray +ve), m/z 400.2 (MH)$^+$; HRMS (ESI): m/z calcd for $C_{26}H_{42}NO_2$ [M+1]$^+$ 400.3210. found 400.3201.

(Compound 9)

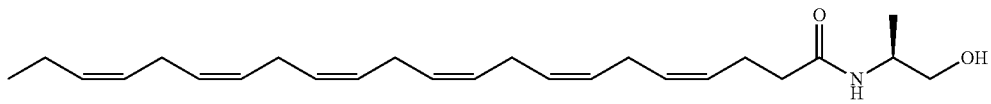

Compound 9, having the formula (4Z,7Z,10Z,13Z,16Z,19Z)—N—((S)-1-hydroxypropan-2-yl)docosa-4,7,10,13,16,19-hexaenamide exhibited the following properties: HPLC: $t_R$=7.35 min, $UV_{254}$=98%; LCMS: (electrospray +ve), m/z 386.3 (MH)$^+$; HRMS (ESI): m/z calcd for $C_{25}H_{39}NO_2Na$ [M+Na]$^+$ 408.2873. found 408.2865.

(Compound 10)

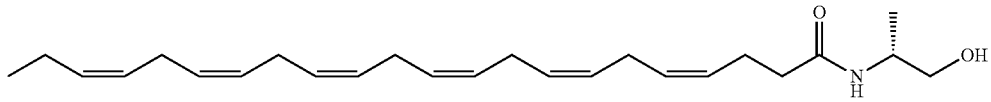

Compound 10, having the formula (4Z,7Z,10Z,13Z,16Z,19Z)—N—((R)-1-hydroxypropan-2-yl)docosa-4,7,10,13,16,19-hexaenamide exhibited the following properties: HPLC: $t_R$=7.35 min, $UV_{254}$=98%; LCMS: (electrospray +ve), m/z 386.3 (MH)$^+$; HRMS (ESI): m/z calcd for $C_{25}H_{39}NO_2Na$ [M+Na]$^+$ 408.2873. found 408.2878.

(Compound 11)

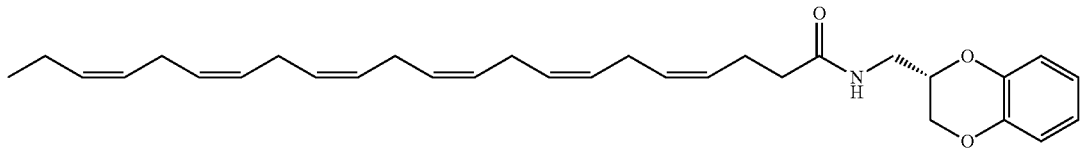

Compound 11, having the formula (4Z,7Z,10Z,13Z,16Z,19Z)—N—(((S)-2,3-dihydrobenzo[b][1,4]dioxin-2-yl)methyl)docosa-4,7,10,13,16,19-hexaenamide exhibited the following properties: HPLC: $t_R$=3.83*min, $UV_{254}$=90%; LCMS: (electrospray +ve), m/z 476.3 (MH)$^+$; HRMS (ESI): m/z calcd for $C_{31}H_{42}NO_3$ [M+1]$^+$ 476.3159. found 476.3171.

(Compound 12)

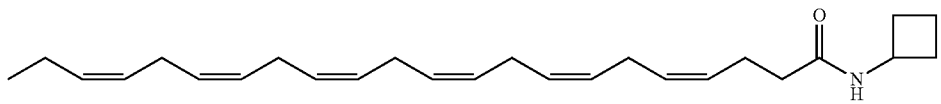

Compound 12, having the formula (4Z,7Z,10Z,13Z,16Z,19Z)—N-cyclobutyldocosa-4,7,10,13,16,19-hexaenamide exhibited the following properties: HPLC: $t_R$=7.86 min, $UV_{254}$=98%; LCMS: (electrospray +ve), m/z 382.4 (MH)$^+$; HRMS (ESI): m/z calcd for $C_{26}H_{40}NO$ [M+1]$^+$ 382.3104. found 382.3094.

(Compound 13)

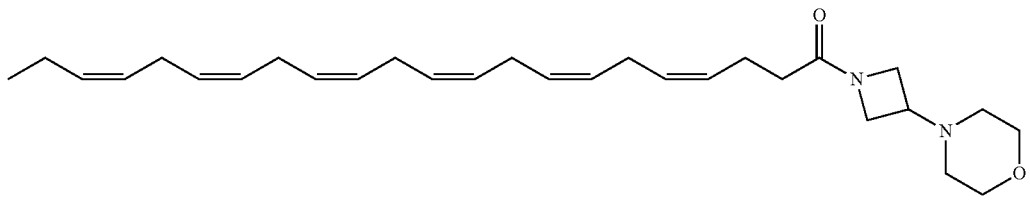

Compound 13, having the formula (4Z,7Z,10Z,13Z,16Z,19Z)-1-(3-morpholinoazetidin-1-yl)docosa-4,7,10,13,16,19-hexaen-1-one exhibited the following properties: HPLC: $t_R$=6.19 min, $UV_{254}$=98%; LCMS: (electrospray +ve), m/z 453.3 (MH)$^+$; HRMS (ESI): m/z calcd for $C_{29}H_{45}N_2O_2$ [M+1]$^+$ 453.3476. found 453.3481.

(Compound 14)

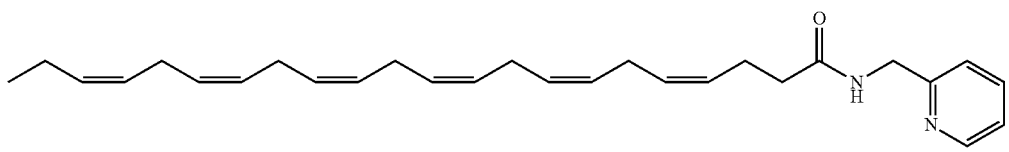

Compound 14, having the formula (4Z,7Z,10Z,13Z,16Z,19Z)—N-(pyridin-2-ylmethyl)docosa-4,7,10,13,16,19-hexaenamide exhibited the following properties: HPLC: $t_R$=2.79*min, $UV_{254}$=95%; LCMS: (electrospray +ve), m/z 419.3 (MH)$^+$; HRMS (ESI): m/z calcd for $C_{28}H_{39}N_2O$ [M+1]$^+$ 419.3057. found 419.3063.

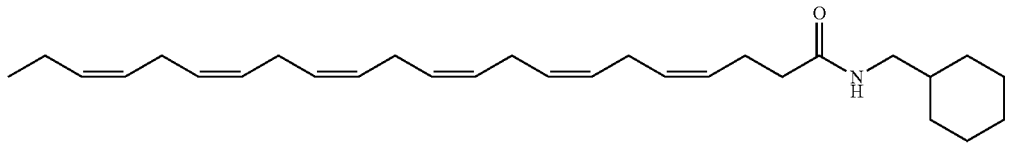
(Compound 15)

Compound 15, having the formula (4Z,7Z,10Z,13Z,16Z,19Z)—N-(cyclohexylmethyl)docosa-4,7,10,13,16,19-hexaenamide exhibited the following properties: HPLC: $t_R$=8.21 min, $UV_{254}$=98%; LCMS: (electrospray +ve), m/z 424.4 (MH)$^+$; HRMS (ESI): m/z calcd for $C_{29}H_{46}NO$ [M+1]$^+$ 424.3574. found 424.3570.

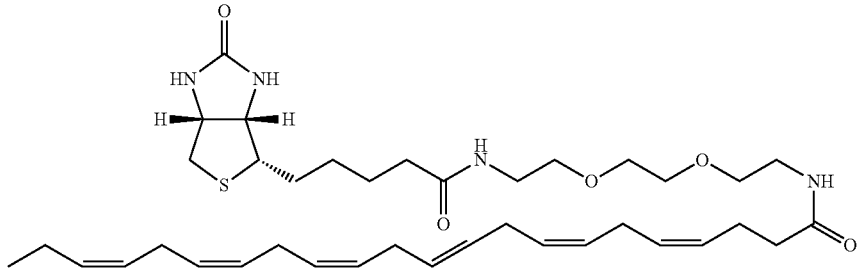
(Compound 16)

Compound 16, having the formula (4Z,7Z,10Z,13Z,16Z,19Z)—N-(2-(2-(2-(5-((3aS,4S,6aR)-2-oxohexahydro-1H-thieno[3,4-d]imidazol-4-yl)pentanamido)ethoxy)ethoxy)ethyl)docosa-4,7,10,13,16,19-hexaenamide exhibited the following properties: HPLC: $t_R$=6.83 min, $UV_{254}$=90%; LCMS: (electrospray +ve), m/z 685.4 (MH)$^+$; HRMS (ESI): m/z calcd for $C_{38}H_{61}N_4O_5S$ [M+1]$^+$ 685.4357. found 685.4380.

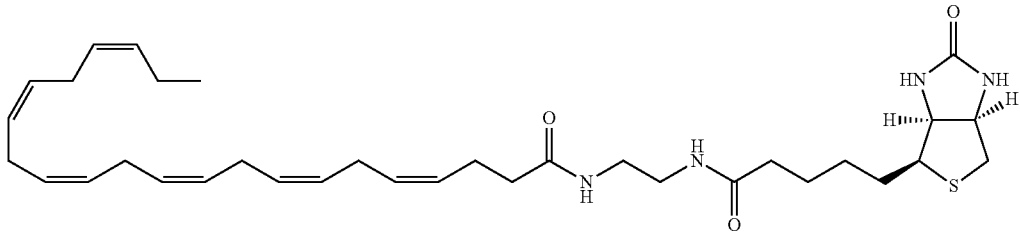
(Compound 17)

Compound 17, having the formula (4Z,7Z,10Z,13Z,16Z,19Z)—N-(2-(5-((3aS,4S,6aR)-2-oxohexahydro-1H-thieno[3,4-d]imidazol-4-yl)pentanamido)ethyl)docosa-4,7,10,13,16,19-hexaenamide exhibited the following properties: HPLC: $t_R$=6.83 min, $UV_{254}$=90%; LCMS: (electrospray +ve), m/z 597.4 (MH)$^+$; HRMS (ESI): m/z calcd for $C_{34}H_{53}N_4O_3S$ [M+1]$^+$, 597.3833. found 597.3828.

(Compound 18)

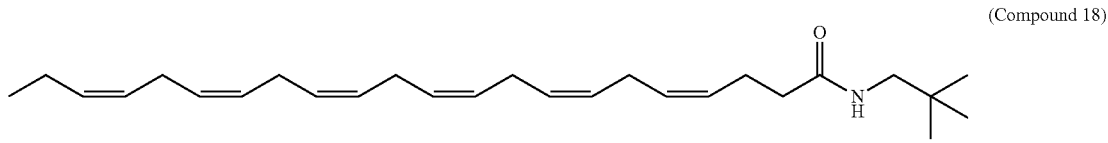 [SMILES: CC/C=C\C/C=C\C/C=C\C/C=C\C/C=C\C/C=C\CCC(=O)NCC(C)(C)C]

Compound 18, having the formula: (4Z,7Z,10Z,13Z,16Z,19Z)—N-neopentyldocosa-4,7,10,13,16,19-hexaenamide exhibited the following properties: HPLC: $t_R$=8.06 min, $UV_{254}$=99%; LCMS: (electrospray +ve), m/z 398.3 (MH)$^+$; HRMS (ESI): m/z calcd for $C_{27}H_{44}NO$ [M+1]$^+$ 398.3417. found 398.3416.

(Compound 19)

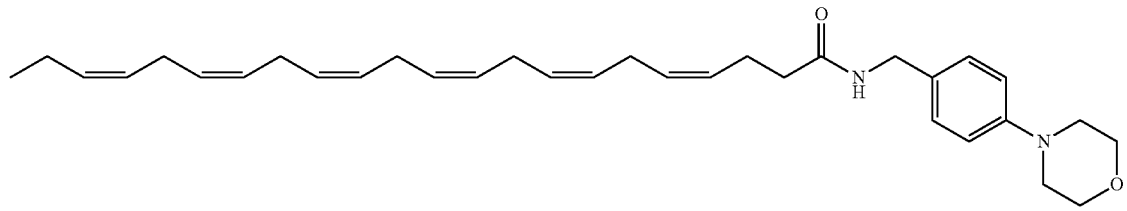

Compound 19, having the formula: (4Z,7Z,10Z,13Z,16Z,19Z)—N-(4-morpholinobenzyl)docosa-4,7,10,13,16,19-hexaenamide exhibited the following properties: HPLC: $t_R$=7.50 min, $UV_{254}$=99%; LCMS: (electrospray +ve), m/z 503.4 (MH)$^+$; HRMS (ESI): m/z calcd for $C_{33}H_{47}N_2O_2$ [M+1]$^+$ 503.3632. found 503.3630.

(Compound 20)

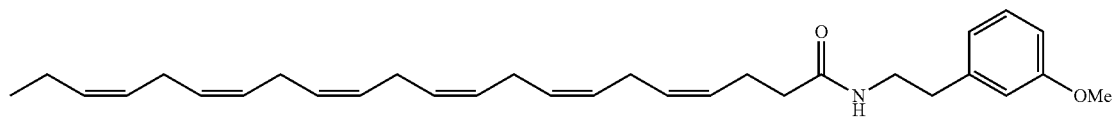

Compound 20, having the formula: (4Z,7Z,10Z,13Z,16Z,19Z)—N-(3-methoxyphenethyl)docosa-4,7,10,13,16,19-hexaenamide exhibited the following properties: HPLC: $t_R$=7.96 min, $UV_{254}$=99%; LCMS: (electrospray +ve), m/z 462.3 (MH)$^+$; HRMS (ESI): m/z calcd for $C_{31}H_{44}NO_2$ [M+1]$^+$ 462.3367. found 462.3356.

(Compound 21)

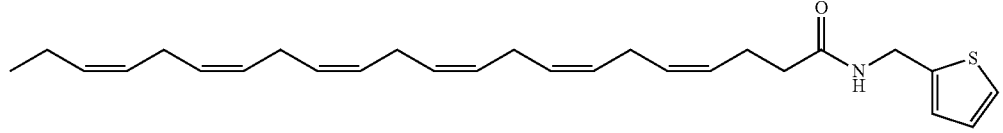

Compound 21, having the formula: (4Z,7Z,10Z,13Z,16Z,19Z)—N-(thiophen-2-ylmethyl)docosa-4,7,10,13,16,19-hexaenamide exhibited the following properties: HPLC: $t_R$=7.89 min, $UV_{254}$=99%; LCMS: (electrospray +ve), m/z 424.3 (MH)$^+$.

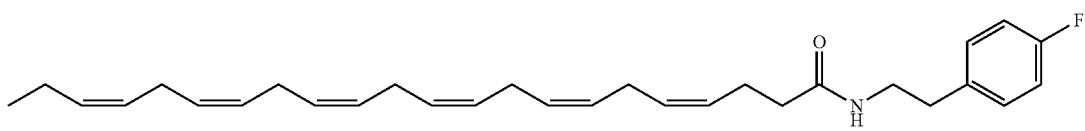
(Compound 22)

Compound 22, having the formula: (4Z,7Z,10Z,13Z,16Z,19Z)—N-(4-fluorophenethyl)docosa-4,7,10,13,16,19-hexaenamide exhibited the following properties: HPLC: $t_R$=7.96 min, $UV_{254}$=99%; LCMS: (electrospray +ve), m/z 450.4 (MH)$^+$; HRMS (ESI): m/z calcd for $C_{30}H_{41}NOF$ [M+1]$^+$ 450.3167. found 450.3619.

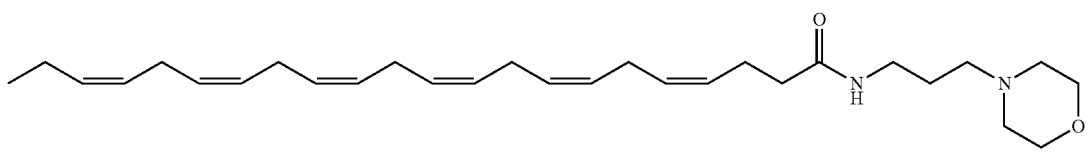
(Compound 23)

Compound 23, having the formula: (4Z,7Z,10Z,13Z,16Z,19Z)—N-(3-morpholinopropyl)docosa-4,7,10,13,16,19-hexaenamide exhibited the following properties: HPLC: $t_R$=6.22 min, $UV_{254}$=99%; LCMS: (electrospray +ve), m/z 455.3 (MH)$^+$.

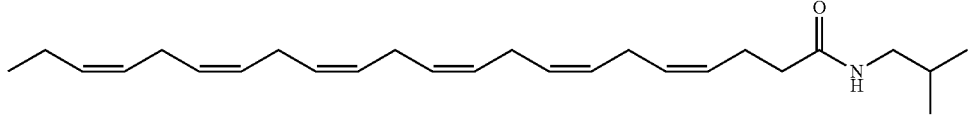
(Compound 24)

Compound 24, having the formula: (4Z,7Z,10Z,13Z,16Z,19Z)—N-isobutyldocosa-4,7,10,13,16,19-hexaenamide exhibited the following properties: HPLC: $t_R$=7.95 min, $UV_{254}$=99%; LCMS: (electrospray +ve), m/z 384.3 (MH)$^+$.

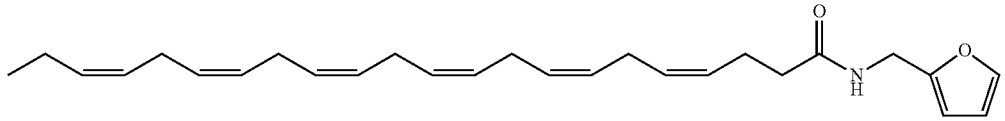
(Compound 25)

Compound 25, having the formula: (4Z,7Z,10Z,13Z,16Z,19Z)—N-(furan-2-ylmethyl)docosa-4,7,10,13,16,19-hexaenamide (25): HPLC: $t_R$=7.79 min, $UV_{254}$=99%; LCMS: (electrospray +ve), m/z 408.2 (MH)⁺.

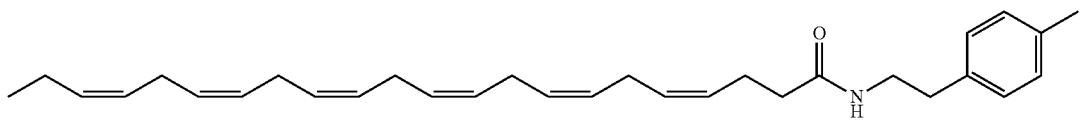
(Compound 26)

Compound 26, having the formula: (4Z,7Z,10Z,13Z,16Z,19Z)—N-(4-methylphenethyl)docosa-4,7,10,13,16,19-hexaenamide exhibited the following properties: HPLC: $t_R$=8.10 min, $UV_{254}$=99%; LCMS: (electrospray +ve), m/z (MH)⁺;446.3.

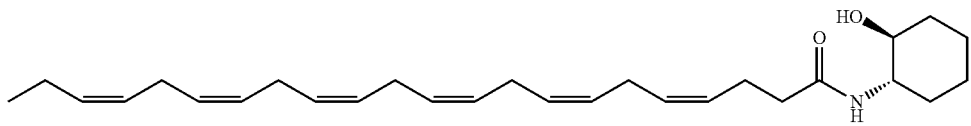
(Compound 27)

Compound 27, having the formula: (4Z,7Z,10Z,13Z,16Z,19Z)—N-((1S,2S)-2-hydroxycyclohexyl)docosa-4,7,10,13,16,19-hexaenamide exhibited the following properties: HPLC: $t_R$=7.64 min, $UV_{254}$=99%; LCMS: (electrospray +ve), m/z 426.4 (MH)⁺; HRMS (ESI): m/z calcd for $C_{28}H_{43}NO_2$ [M+1]⁺ 426.3367. found 426.3377.

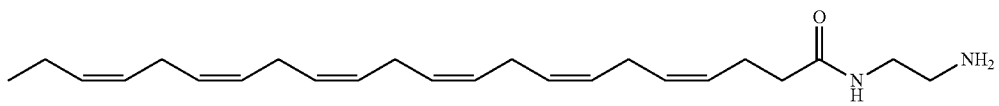
(Compound 28)

Compound 28, having the formula: (4Z,7Z,10Z,13Z,16Z,19Z)—N-(2-aminoethyl)docosa-4,7,10,13,16,19-hexaenamide exhibited the following properties: HPLC: $t_R$=5.99 min, $UV_{254}$=99%; LCMS: (electrospray +ve), m/z 371.4 (MH)⁺.

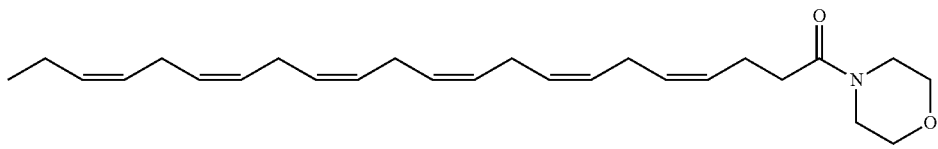
(Compound 29)

Compound 29, having the formula: (4Z,7Z,10Z,13Z,16Z,19Z)-1-morpholinodocosa-4,7,10,13,16,19-hexaen-1-one exhibited the following properties: HPLC: $t_R$=7.77 min, $UV_{254}$=98%; LCMS: (electrospray +ve), m/z 398.3 (MH)⁺; HRMS (ESI): m/z calcd for $C_{26}H_{40}NO_2$ [M+1]⁺ 398.3054. found 398.3058.

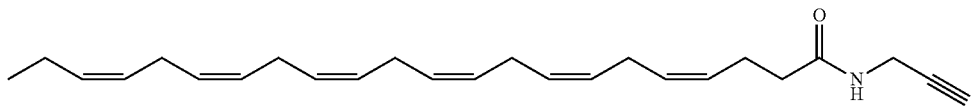

(Compound 30)

Compound 30, having the formula: (4Z,7Z,10Z,13Z,16Z,19Z)—N-(prop-2-ynyl)docosa-4,7,10,13,16,19-hexaenamide exhibited the following properties: HPLC: $t_R$=7.64 min, $UV_{254}$=98%; LCMS: (electrospray +ve), m/z 366.3 (MH)$^+$; HRMS (ESI): m/z calcd for $C_{25}H_{36}NO$ [M+1]$^+$ 366.2791. found 366.2779.

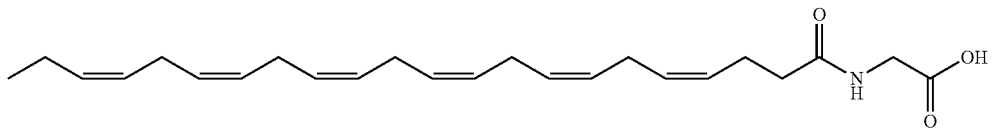

(Compound 31)

Compound 31, having the formula: 2-(4Z,7Z,10Z,13Z,16Z,19Z)-docosa-4,7,10,13,16,19-hexaenamidoacetic acid exhibited the following properties: HPLC: $t_R$=8.10 min, $UV_{254}$=99%; LCMS: (electrospray +ve), m/z 385.4 (MH)$^+$.

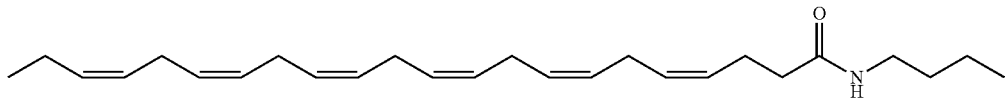

(Compound 32)

Compound 32, having the formula: (4Z,7Z,10Z,13Z,16Z,19Z)—N-butyldocosa-4,7,10,13,16,19-hexaenamide (32): HPLC: $t_R$=7.95 min, $UV_{254}$=98%; LCMS: (electrospray +ve), m/z 384.3 (MH)$^+$.

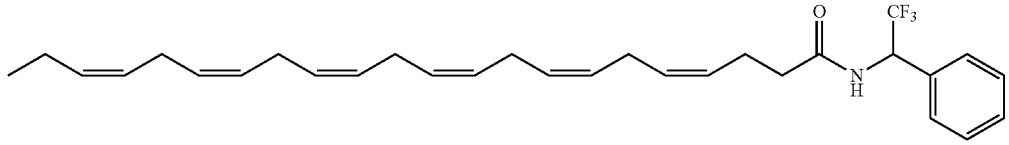

(Compound 33)

Compound 33, having the formula: (4Z,7Z,10Z,13Z,16Z,19Z)—N-(2,2,2-trifluoro-1-phenylethyl)docosa-4,7,10,13,16,19-hexaenamide exhibited the following properties: HPLC: $t_R$=8.06 min, $UV_{254}$=98%; LCMS: (electrospray +ve), m/z 486.3 (MH)$^+$.

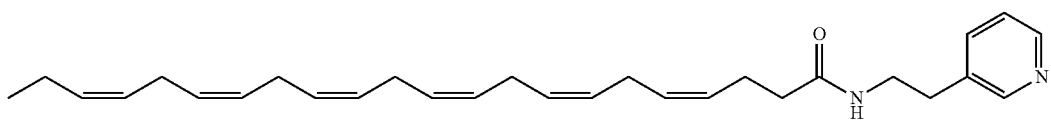

(Compound 34)

Compound 34, having the formula: (4Z,7Z,10Z,13Z,16Z,19Z)—N-(2-(pyridin-3-yl)ethyl)docosa-4,7,10,13,16,19-hexaenamide exhibited the following properties: HPLC: $t_R$=2.69*min, $UV_{254}$=95%; LCMS: (electrospray +ve), m/z 433.4 (MH)$^+$; HRMS (ESI): m/z calcd for $C_{29}H_{41}N_2O$ [M+1]$^+$ 433.3213. found 433.3221.

(Compound 35)

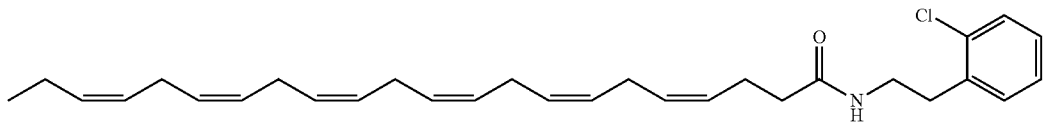

Compound 35, having the formula: (4Z,7Z,10Z,13Z,16Z,19Z)—N-(2-chlorophenethyl)docosa-4,7,10,13,16,19-hexaenamide exhibited the following properties: HPLC: $t_R$=8.10 min, $UV_{254}$=98%; LCMS: (electrospray +ve), m/z 467.3 (MH)$^+$; HRMS (ESI): m/z calcd for $C_{30}H_{41}NOCl$ [M+1]$^+$ 466.2871. found 466.2872.

(Compound 36)

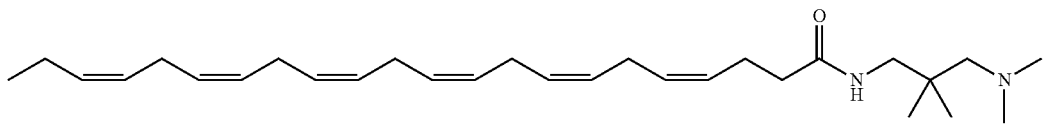

Compound 36, having the formula: (4Z,7Z,10Z,13Z,16Z,19Z)—N-(3-(dimethylamino)-2,2-dimethylpropyl)docosa-4,7,10,13,16,19-hexaenamide exhibited the following properties: HPLC: $t_R$=2.78*min, $UV_{254}$=95%; LCMS: (electrospray +ve), m/z 441.4 (MH)$^+$; HRMS (ESI): m/z calcd for $C_{29}H_{49}N_2O$ [M+1]$^+$ 441.3839. found 441.3841.

(Compound 37)

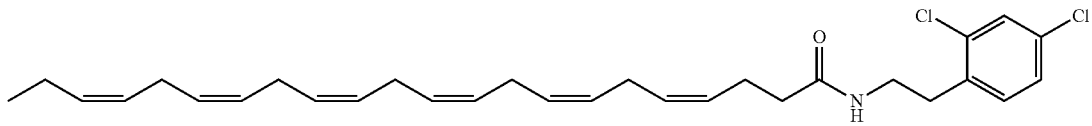

Compound 37, having the formula: (4Z,7Z,10Z,13Z,16Z,19Z)—N-(2,4-dichlorophenethyl)docosa-4,7,10,13,16,19-hexaenamide exhibited the following properties: HPLC: $t_R$=8.27 min, $UV_{254}$=98%; LCMS: (electrospray +ve), m/z 501.2 (MH)$^+$; HRMS (ESI): m/z calcd for $C_{30}H_{40}NOCl_2$ [M+1]$^+$ 500.2460. found 500.2467.

(Compound 38)

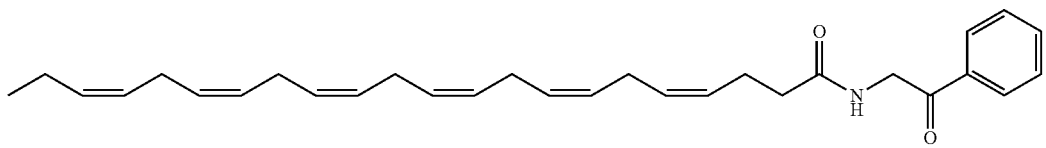

Compound 38, having the formula: (4Z,7Z,10Z,13Z,16Z,19Z)—N-(2-oxo-2-phenylethyl)docosa-4,7,10,13,16,19-hexaenamide exhibited the following properties: HPLC: $t_R$=7.88 min, $UV_{254}$=95%; LCMS: (electrospray +ve), m/z 446.3 (MH)$^+$; HRMS (ESI): m/z calcd for $C_{30}H_{40}NO_2$ [M+1]$^+$ 446.3054. found 446.3061.

(Compound 39)

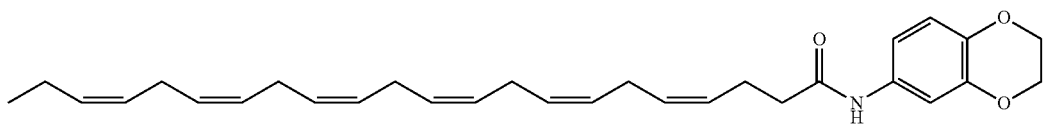

Compound 39, having the formula: (4Z,7Z,10Z,13Z,16Z, 19Z)—N-(2,3-dihydrobenzo[b][1,4]dioxin-6-yl)docosa-4,7, 10,13,16,19-hexaenamide exhibited the following properties: HPLC: $t_R$=3.82*min, $UV_{254}$=98%; LCMS: (electrospray +ve), m/z 462.3 $(MH)^+$; HRMS (ESI): m/z calcd for $C_{30}H_{40}NO_3$ $[M+1]^+$ 462.3003. found 462.2998.

(Compound 40)

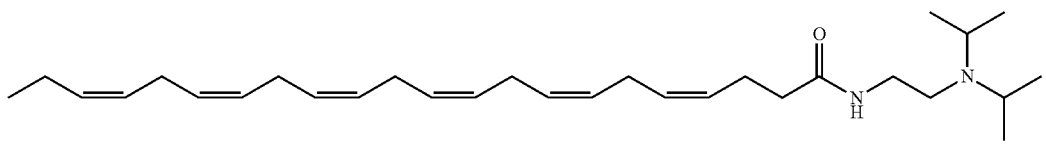

Compound 40, having the formula: (4Z,7Z,10Z,13Z,16Z, 19Z)—N-(2-(diisopropylamino)ethyl)docosa-4,7,10,13,16, 19-hexaenamide exhibited the following properties: HPLC: $t_R$=6.59 min, $UV_{254}$=98%; LCMS: (electrospray +ve), m/z 455.4 $(MH)^+$; HRMS (ESI): m/z calcd for $C_{30}H_{51}N_2O$ $[M+1]^+$ 455.3996. found 455.3998.

(Compound 41)

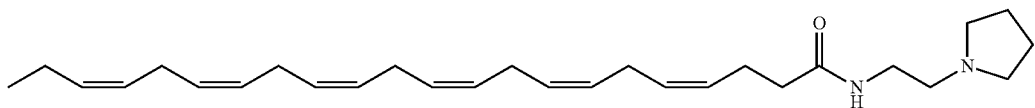

Compound 41, having the formula: (4Z,7Z,10Z,13Z,16Z, 19Z)—N-(2-(pyrrolidin-1-yl)ethyl)docosa-4,7,10,13,16,19-hexaenamide exhibited the following properties: HPLC: $t_R$=2.72*min, $UV_{254}$=95%; LCMS: (electrospray +ve), m/z 425.4 $(MH)^+$; HRMS (ESI): m/z calcd for $C_{28}H_{45}N_2O$ $[M+1]^+$ 425.3526. found 425.3513.

(Compound 42)

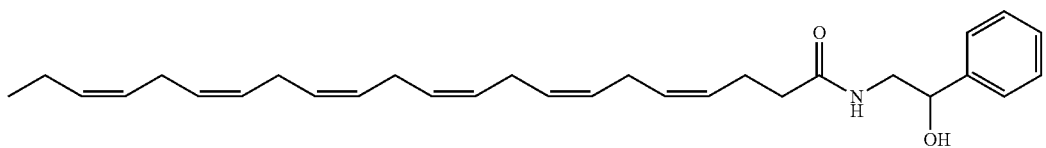

Compound 42, having the formula: (4Z,7Z,10Z,13Z,16Z,19Z)—N-(2-hydroxy-2-phenylethyl)docosa-4,7,10,13,16,19-hexaenamide exhibited the following properties: HPLC: $t_R$=7.70 min, $UV_{254}$=99%; LCMS: (electrospray +ve), m/z 448.3 (MH)$^+$; HRMS (ESI): m/z calcd for $C_{30}H_{42}NO_2$ [M+1]$^+$ 448.3210. found 448.3213.

(Compound 43)

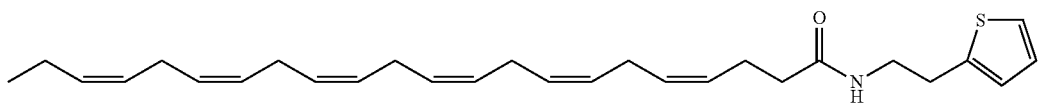

Compound 43, having the formula: (4Z,7Z,10Z,13Z,16Z,19Z)—N-(2-(thiophen-2-yl)ethyl)docosa-4,7,10,13,16,19-hexaenamide exhibited the following properties: HPLC: $t_R$=3.82*min, $UV_{254}$=95%; LCMS: (electrospray +ve), m/z 438.3 (MH)$^+$; HRMS (ESI): m/z calcd for $C_{28}H_{40}NOS$ [M+1]$^+$ 438.2825. found 438.2807.

(Compound 44)

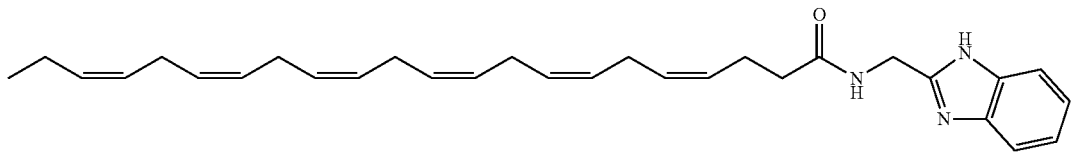

Compound 44, having the formula: (4Z,7Z,10Z,13Z,16Z,19Z)—N-((1H-benzo[d]imidazol-2-yl)methyl)docosa-4,7,10,13,16,19-hexaenamide exhibited the following properties: HPLC: $t_R$=6.40 min, $UV_{254}$=99%; LCMS: (electrospray +ve), m/z 458.3 (MH)$^+$; HRMS (ESI): m/z calcd for $C_{30}H_{40}N_3O$ [M+1]$^+$ 458.3166. found 458.3159.

(Compound 45)

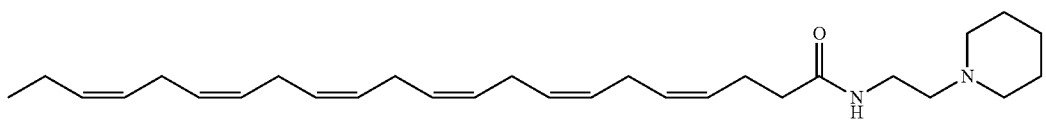

Compound 45, having the formula: (4Z,7Z,10Z,13Z,16Z,19Z)—N-(2-(piperidin-1-yl)ethyl)docosa-4,7,10,13,16,19-hexaenamide (45): HPLC: $t_R$=6.43 min, $UV_{254}$=95%; LCMS: (electrospray +ve), m/z 439.3 (MH)$^+$; HRMS (ESI): m/z calcd for $C_{29}H_{47}N_2O$ [M+1]$^+$ 439.3683. found 439.3697.

(Compound 46)

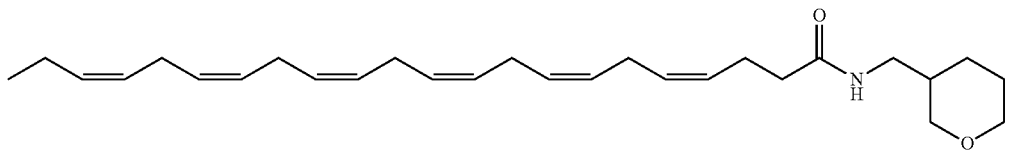

Compound 46, having the formula: (4Z,7Z,10Z,13Z,16Z,19Z)—N-((tetrahydro-2H-pyran-3-yl)methyl)docosa-4,7,10,13,16,19-hexaenamide exhibited the following properties: HPLC: $t_R$=3.66*min, $UV_{254}$=98%; LCMS: (electrospray +ve), m/z 426.4 (MH)$^+$; HRMS (ESI): m/z calcd for $C_{28}H_{44}NO_2$ [M+1]$^+$ 426.3367. found 426.3357.

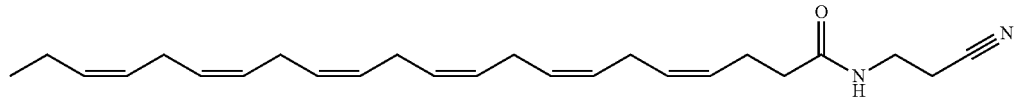

(Compound 47)

Compound 47, having the formula: (4Z,7Z,10Z,13Z,16Z,19Z)—N-(2-cyanoethyl)docosa-4,7,10,13,16,19-hexaenamide exhibited the following properties: HPLC: $t_R$=7.50 min, $UV_{254}$=99%; LCMS: (electrospray +ve), m/z 381.4 (MH)$^+$; HRMS (ESI): m/z calcd for $C_{25}H_{37}N_2O$ [M+1]$^+$ 381.2900. found 381.2913.

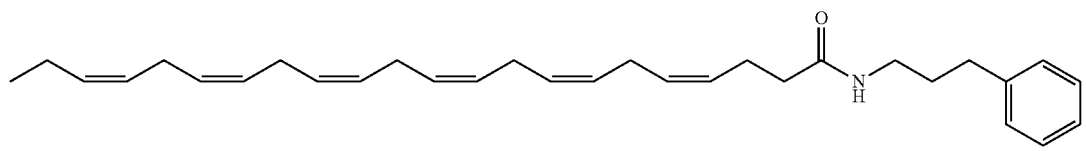

(Compound 48)

Compound 48, having the formula: (4Z,7Z,10Z,13Z,16Z,19Z)—N-(3-phenylpropyl)docosa-4,7,10,13,16,19-hexaenamide exhibited the following properties: HPLC: $t_R$=8.05 min, $UV_{254}$=98%; LCMS: (electrospray +ve), m/z 446.4 (MH)$^+$; HRMS (ESI): m/z calcd for $C_{31}H_{44}NO$ [M+1]$^+$ 446.3417. found 446.3421.

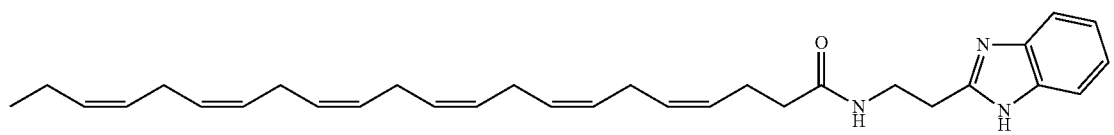

(Compound 49)

Compound 49, having the formula: (4Z,7Z,10Z,13Z,16Z,19Z)—N-(2-(1H-benzo[d]imidazol-2-yl)ethyl)docosa-4,7,10,13,16,19-hexaenamide exhibited the following properties: HPLC: $t_R$=6.46 min, $UV_{254}$=95%; LCMS: (electrospray +ve), m/z 472.3 (MH)$^+$; HRMS (ESI): m/z calcd for $C_{31}H_{42}N_3O$ [M+1]$^+$, 472.3322. found 472.3323.

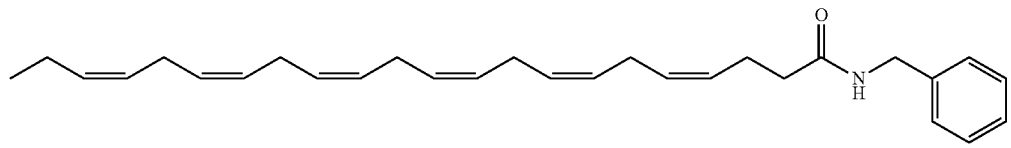

(Compound 50)

Compound 50, having the formula: (4Z,7Z,10Z,13Z,16Z, 19Z)—N-benzyldocosa-4,7,10,13,16,19-hexaenamide exhibited the following properties: HPLC: $t_R$=3.79*min, $UV_{254}$=95%; LCMS: (electrospray +ve), m/z 418.3 (MH)$^+$; HRMS (ESI): m/z calcd for $C_{29}H_{40}NO$ [M+1]$^+$ 418.3104. found 418.3124.

Example 2

This example demonstrates analysis of effects of synaptamide derivatives as prepared in Example 1 (Compounds 1-50) on neurite growth.

To obtain embryonic mouse neurons for analysis, pregnant female mice were killed by cervical dislocation after exposure to $CO_2$ inhalation. Embryonic neurons were prepared from E18 or P0 mouse hippocampi or cortex and cultured as described previously (Calderon and Kim, *J. Neurochem.*, 90(4):979-88 (2004), errata in *J Neurochem.*, September; 90(6):1540 (2004)), with slight modification. Briefly, hippocampi or cotices were dissected and dissociated by a method using either 0.25% trypsin (Gibco Invitrogen Corporation, Grand Island, N.Y.) in Hank's balanced salt solution (HBSS) or papain (20-30 U/mL) in dissociation media containing cysteine at 37° C. for 15 min. After the dissociation solution was aspirated off, cells were washed with same volume of HBSS, suspended in neurobasal medium (Gibco) containing 2% B27 supplement (Gibco), 1% glutamine/glutamax mix (1:4) (Gibco), 100 U/ml penicillin (Gibco) and 100 μg/ml streptomycin (Gibco), and seeded on poly-D-lysine chambered slides (Lab-Tek, Naperville, Ill.) at a density of 30,000 cells/cm$^2$. On the second day after seeding, the cells were treated with fatty acids, synaptamide or one of Compounds 1-50 for 48 h. Docosahexaenoic acid (DHA) and oleic acid (OA) were complexed with fatty acid-free bovine serum albumin (BSA; Sigma, St Louis, Mo.) in the presence of α-tocopherol (Sigma) under an argon atmosphere and darkness to prevent oxidation of the fatty acids. The mixture was mixed with fresh Neurobasal medium containing B27 supplement, glutamine/glutamax mix and antibiotics. Final concentrations of α-tocopherol and BSA in the culture medium were 40 μM and 0.01%, respectively. Alternatively, DHA, OA, synaptamide, or one of Compounds 1-50 were dissolved in DMSO and applied directly together with α-tocopherol. In such case, the final concentration of DMSO is less than 0.005%. All stock solutions were aliquoted under argon and stored at –70° C.

Cells were fixed with 0.4% paraformaldehyde (Sigma) in PBS (pH 7.4) for 30 min. After permeabilization with 0.1% Triton X-100 (Sigma), cells were blocked for 1 h at 37° C. with PBS containing 10% goat serum (Gibco), and then incubated with the primary antibody against microtubule-associated protein (MAP2, mouse monoclonal 1:250; Sigma). After washing with PBS, cells were incubated with the corresponding Cy2-, Cy3-conjugated secondary antibody (Jackson Immunoresearch Laboratories Inc., West Grove, Pa.). For the nuclear staining, 0.06% 4,6-Diamidino-2-Phenylindole (Sigma) was used. After immunostaining, images were collected using an inverted motorized 1×81 Olympus (Melville, N.Y.) and the neurite length was analyzed with Metamorph software (Molecular Devices Corporation, Downingtown, Pa.). To minimize bias, neurons were evaluated blindly without the knowledge of sample identity. Four to six fields/well were chosen at random and only non-clustered neurons were evaluated to ensure the precision of the measurements. From each well, over 100 neurons were evaluated at 20× magnification for total neurite length/neuron. The data were obtained from triplicate wells and the experiments were repeated at least three times.

Results of these experiments for Compounds 1-10 applied to the cortical neurons are provided in Table 2.

TABLE 2

| | | | | Neurite Length/ Neuron (μm) | SE |
|---|---|---|---|---|---|
| Control | 4.7 | 3.5 | 3.3 | 3.8 | 0.4 |
| DHA | 10.9 | 19.4 | 13.3 | 14.5 | 2.5 |
| Synaptamide | 33.1 | 29.2 | 25.5 | 29.3 | 2.2 |
| A1 | 10.9 | 9.5 | 6.8 | 9.1 | 1.2 |
| A2 | 14.0 | 2.4 | 12.4 | 9.6 | 3.6 |
| A3 | 14.2 | 5.8 | 8.5 | 9.5 | 2.5 |
| A4 | 2.9 | 4.1 | 4.3 | 3.8 | 0.4 |
| A5 | 4.5 | 10.2 | 5.3 | 6.7 | 1.8 |
| A6 | 3.6 | 4.6 | 5.4 | 4.5 | 0.5 |
| A7 | 7.6 | 7.4 | 5.8 | 6.9 | 0.6 |
| A8 | 45.0 | 33.6 | 45.3 | 41.3 | 3.9 |
| A9 | 30.1 | 56.3 | 38.9 | 41.8 | 7.7 |
| A10 | 13.4 | 27.6 | 21.5 | 20.8 | 4.1 |

Figure 2:
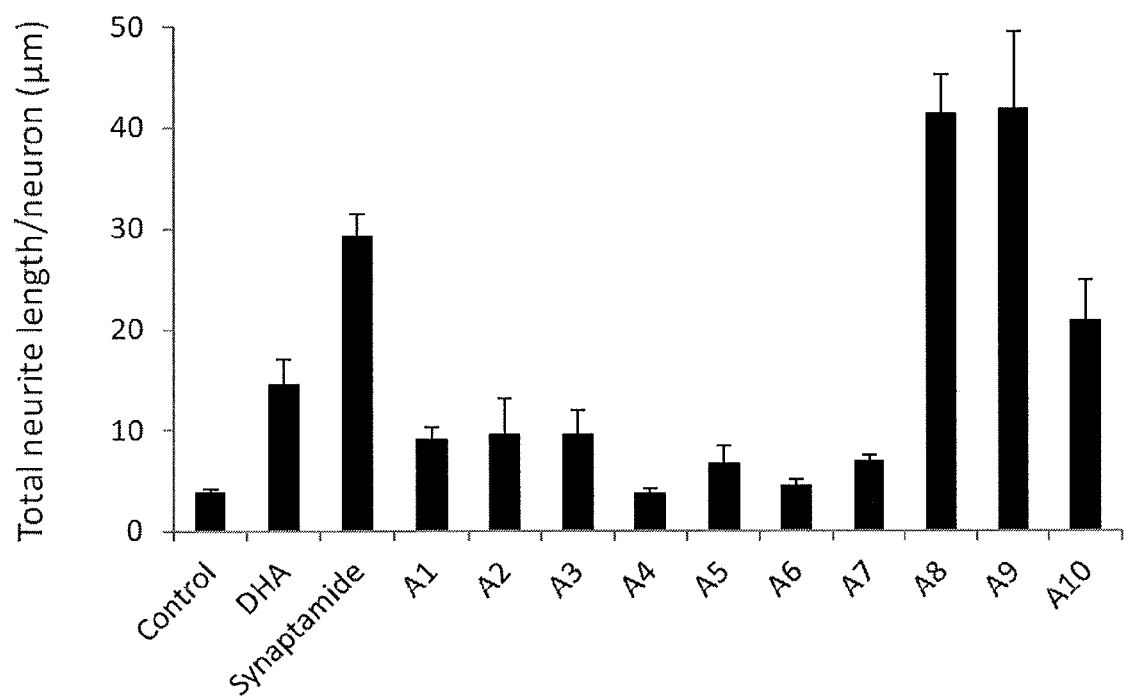
FIG. 2 is a plot of total neurite length per neuron (μm) for neurons treated with 10 nM synaptamide derivatives A1-A10 as compared to DHA (100 nM), DEA (synaptamide, 10 nM), and a negative control, in accordance with embodiments of the invention. Figures are mean total neurite length per neuron for approximately 40 neurons from three randomly selected fields.
Figure 3:
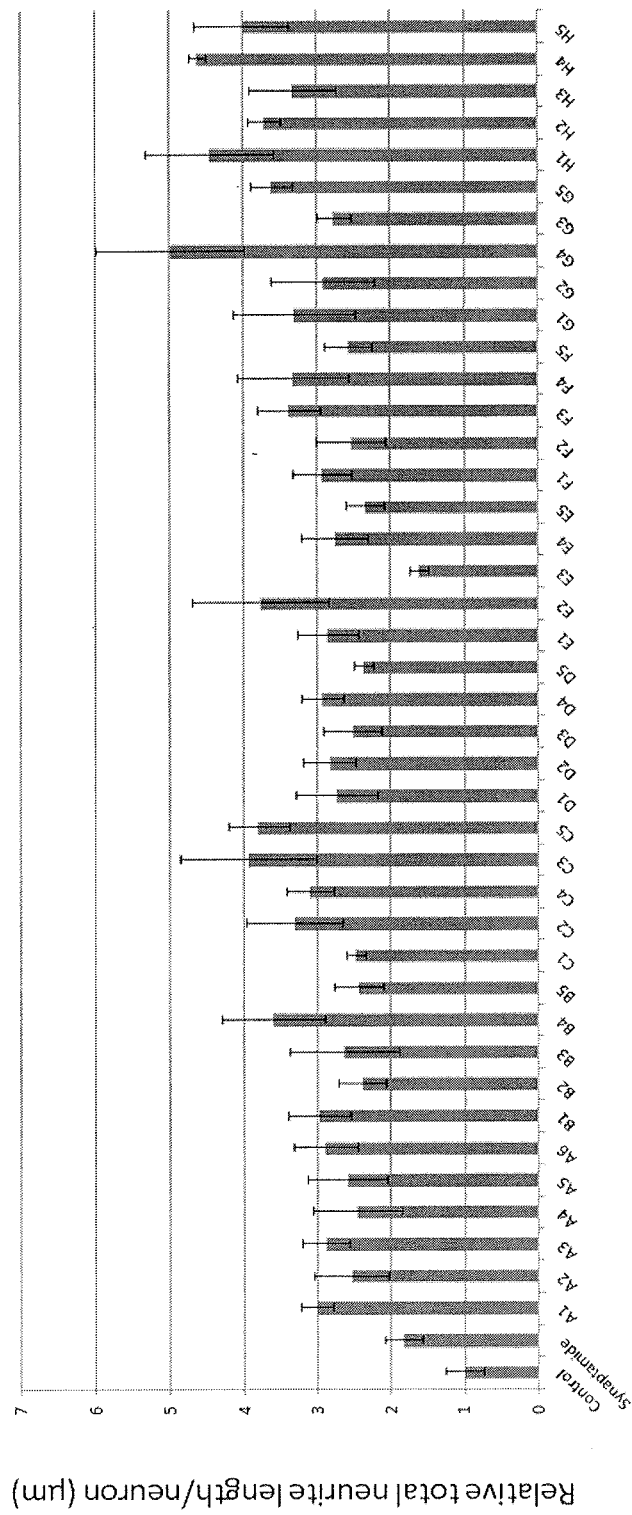
FIG. 3 is a plot of relative total neurite outgrowth per neuron as compared to a negative control (relative total outgrowth of control=1), for DEA derivatives A1-A6, B1-B5, C1-C5, D1-D5, E1-E5, F1-F5, G1-G5, and H1-H5, in accordance with embodiments of the invention.
Figure 4:
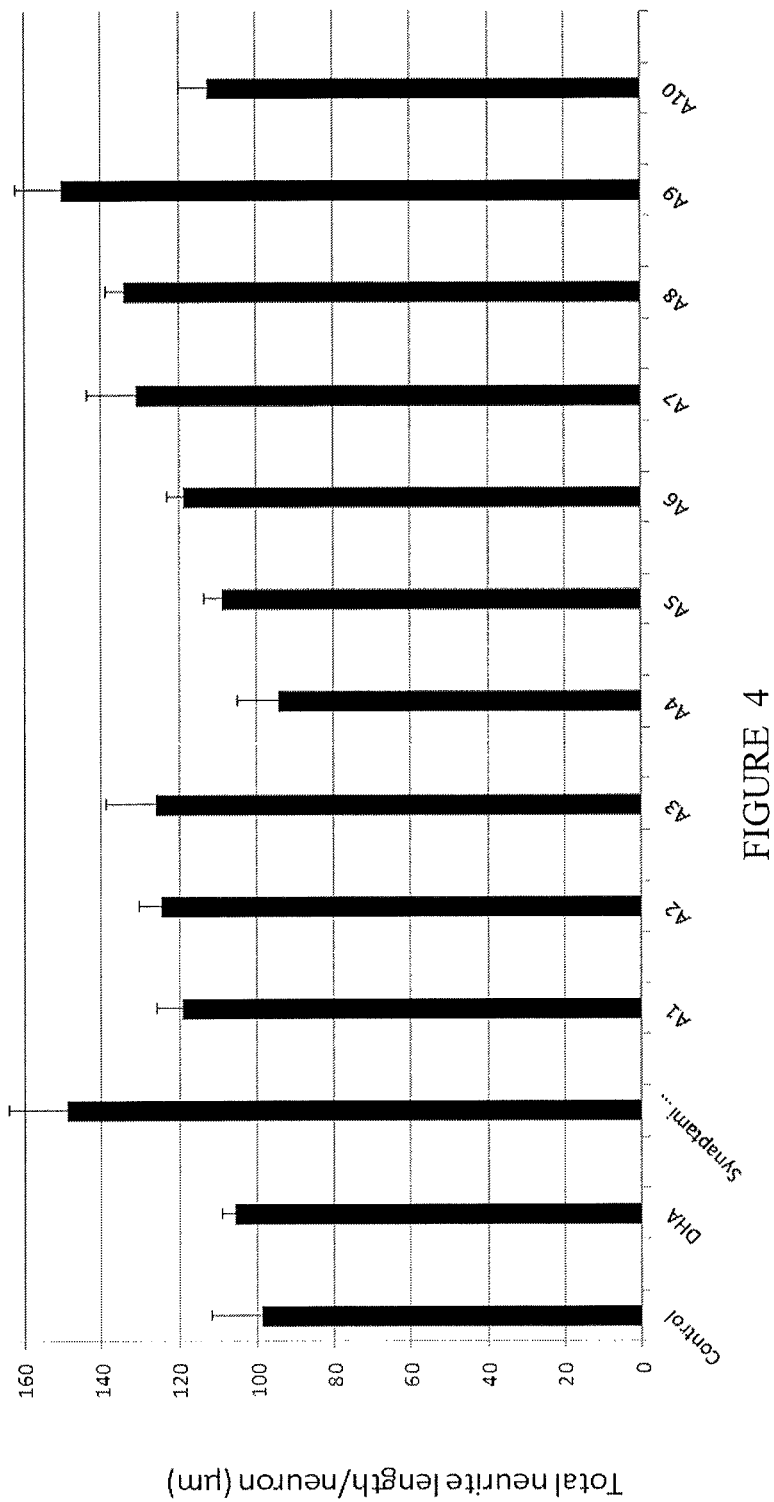
FIG. 4 is a plot of neurite outgrowth in hippocampal neurons (DIV 1), expressed in terms of average total neurite length per neuron for neurons treated with 10 nM synaptamide derivatives A1-A10 as compared to DHA, DEA (synaptamide, 100 nM), for 72 hours, in accordance with embodiments of the invention.
Figure 5:
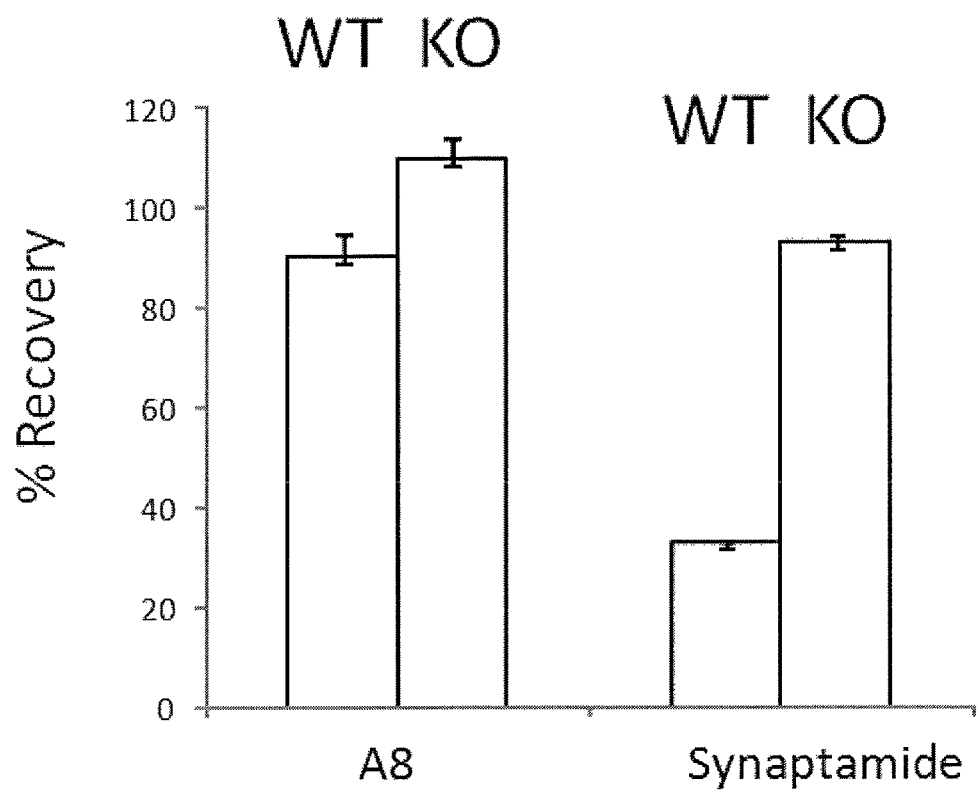
FIG. 5 is a plot of percent recovery of compound (A8 or synaptamide) after incubation of wildtype (WT) or fatty acid amide hydrolase (FAAH) knock out (KO) brain homogenate with compound, in accordance with embodiments of the invention.

FIG. 2 provides graphical results of the data shown in Table 2, expressed as total neurite length per neuron. FIG. 3 provides graphical results of these experiments for compounds 11-50 (having designations as provided in Table 1, above), expressed as relative neurite length as compared to untreated controls. FIG. 4 provides graphical results of these experiments for compounds 1-10 (having designations as provided in Table 1, above), as applied to hippocampal neurons.

An additional assay was performed in which Compounds (A8), 4(A10), and 7(A9) were applied at varying dosages (from $10^{-5}$ nM to 10 nM; $10^{-5}$ nM, $10^{-4}$ nM, $10^{-2}$ nM, 0.1 nM, 1 nM, and 10 nM) as compared to DHA, synaptamide, and oleic acid. Neurite growth was measured at each dosage. Results of this assay are provided at FIG. 1.

These results demonstrate that Compounds 11-50 demonstrate comparable or superior effect on relative neurite length as compared to synaptamide. Furthermore, Compounds 1, 7, and 4, identified in FIGS. 1, 2 and 4 as A8, A9, and A10, respectively, provide superior effect with respect to cortical neurite growth as compared to DHA, and exhibit activity at significantly lower dosages as compared to DHA and synaptamide.

Example 3

This Example demonstrates analysis of the stability of A8 of the present invention based on susceptibility to fatty acid amide hydrolase (FAAH) hydrolysis.

Wildtype (WT) or FAAH knock out (KO) brain homogenates were incubated with either A8 or synaptamide. The data of FIG. 5 suggests that the percent recovery of A8 is higher than synaptamide in both WT and FAAH KO samples, which suggests that A8 is less susceptible to hydrolysis by FAAH than synaptamide.

Example 4

This Example also demonstrates analysis of the stability of A8 of the present invention based on susceptibility to FAAH hydrolysis.

Incubation of synaptamide and A8 with brain homogenates: Make 5× pH 9 assay buffer (625 mM Tris, 5 mM EDTA). Collect fresh brains of C57 mice into cold 1× pH 9 assay buffer. Homogenize entire brain (including cerebellum) in 2 mL of cold buffer using a conical Potter-Evehjem type tissue homogenizer driven by a motor. Perform incubations in washed and silanized 10 mL glass test tubes at 37° C. for 1 hour. Add 10 pmoles each of A8 and d4-synaptamide (5 uL of a 2 pmol/uL mixture of A8 and d4-synaptamide in DMSO). See Kim et al., *Prostaglandins & Other Lipid Mediators*, 96(1-4):114-120 (2011) for the structure of d4-synaptamide (d4-DEA). Add 500 µL of brain homogenate per incubation tube. Vortex gently. Incubate at 37° C. in a water bath, shaking at 42 rpm for 1 hour. Stop reaction by adding 1 mL chloroform, 1 mL methanol, 1 mL methanol/BHT (50 mg/L BHT) and 300 µL water. Vortex to mix, store under an inert gas at −80° C. until. Ready to extract via the method of Bligh and Dyer, Canadian J. Biochem. 37: 911-917, 1959.

Extraction procedure: Incubations are already in the 1$^{st}$ Bligh-Dyer ration (0.8:1:2 aqueous:CHCl$_3$:MeOH). Work on wet ice. Add 10 pmoles of d4-anandamide which will be used as an internal standard to give relative quantification of the unhydrolyzed d4-synaptamide and A8. Add 1 mL water and 1 mL CHCl$_3$ to each tube, purge with nitrogen, vortex vigorously 1 minute. Centrifuge 5 minutes at 4° C.; 3,000 rpm (Sorvall RTH 750 rotor) to separate phases. Extract the organic phase (bottom layer) to a clean silanized 10 mL test tube using glass Pasteur pipette. Avoid getting any aqueous phase in extract. Add 2 mL CHCl$_3$ to the aqueous phase, purge with nitrogen and vortex 1 minute. Centrifuge as before and pool the organic phase with previous extract. Repeat extraction one more time using 2 mL CHCl$_3$. Dry the extract under nitrogen, resuspend in 50 microliters 2:1 CHCl$_3$:MeOH. Vortex and spin at 3,000 rpm to get all extract to bottom of test tube. Transfer extract to LC vials (use small volume inserts). Cap vials under argon and store at −80° C. until ready to analyze via HPLC-MS.

HPLC-MS Analysis:
I. HPLC Conditions:
Mobile Phase A: 30% Methanol; 70% Water; 0.1% Acetic acid
Mobile Phase B: 100% Methanol; 0.1% Acetic Acid
Mobile Phase C: 88% methanol; 12% hexane; 0.1% acetic acid
Flow Rate: 0.4 mL/minute
Column: BDS Hypersil C18; 50 mm×2.1 mm (Thermo Scientific P/N 28105-052130)
Method 1 Gradient: 0 minutes: 100% A
  1 minute: 100% B
  7 minutes: 100% B
  7.1 minutes: 100% A
  11.1 minutes: 100% A
Depending on the column used, it may be necessary to have two blank runs (injecting methanol) between actual sample runs in order to ensure that there is no carry-over from run to run. For the first washing step, mobile phase C should be included. For the second washing step, simply run the Method 1 gradient again. For the first washing step, the gradient program is:
Method 2 Gradient: 0 minutes: 100% A
  1 minute: 100% B
  3 minutes: 100% B
  4 minutes: 100% C
  8 minutes: 100% C
  9 minutes: 100% B
  11.1 minutes: 100% B
II. Mass Spec Conditions For HPLC Runs (Thermo Quantum Ultra TSQ; Positive ionization; SRM mode)

Transitions Monitored (0.05 second dwell time per transition)
  352.3→66.2 (d4-anandamide)
  376.3→66.2 (d4-synaptamide)
  400.3→72.2 (A8)
  400.3→382.3 (A8)
Spray Voltage: 4,000
Capillary Temperature: 350° C.
Sheath Gas Pressure: 35
Sweep Gas Pressure: 0
Aux Gas Pressure: 5
Collision Gas Pressure: 1.2 mtorr
Collision Gas Energy: 15

III. Mass Spectrometer Conditions For Direct Infusion Analysis (Thermo Quantum Ultra TSQ): All runs done at 10, then 20, then 40 uL per minute, using a "T" to mix analogs with HPLC solvents running at 0.4 mL per minute, 95% B, 5% A (B=100% MeOH; A=30% MeOH/70% Water; both with 0.1% acetic acid). For A8: From the 25 mg/mL in DMSO stock, made 200 pmol/uL into MeOH for infusion.

The following references use an incubation procedure similar to the one described above (each incorporated by reference with regard to the procedure): Mauro Maccarrone, Monica Bari, and Alessandro Finazzi Agro, "A sensitive and specific radiochromatographic assay of fatty acid amide hydrolase activity," Analytical Biochemistry 267, 314-318 (1999); Mitsunori Kono et. al., "Synthesis, SAR study, and biological evaluation of a series of piperazine ureas as fatty acid amide hydrolase (FAAH) inhibitors," Bioorganic & Medicinal Chemistry 21 (2013) 28-41; and Alexander C. Hayes et. al., "Identification of N-acylethanolamines in *Dictyostelium discoideum* and confirmation of their hydrolysis by fatty acid amide hydrolase," J Lipid Res. 2013 February; 54(2):457-66

Figure 6:
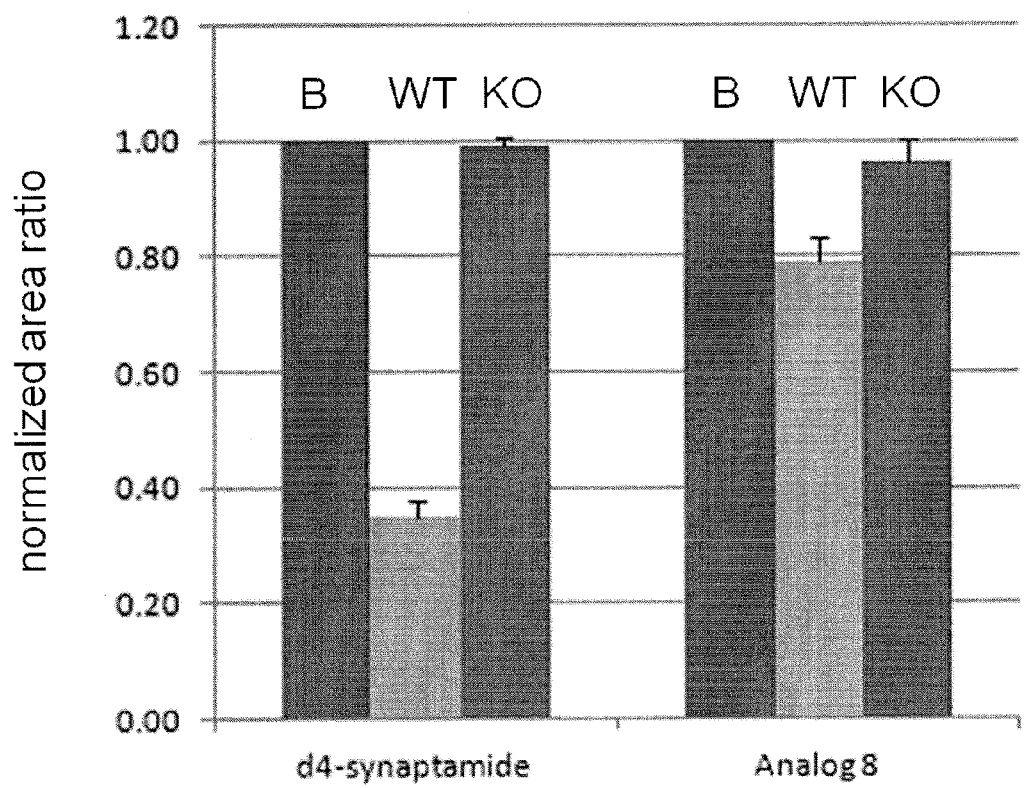
FIG. 6 is a plot of normalized area ratio of compound (Analog 8 (A8) or synaptamide deuterated at four positions) to anandamide (deuterated at four positions), normalized to buffer-only-value, in accordance with embodiments of the invention.

Ten pmoles each of A8 and d4-synaptamide were incubated with WT or FAAH KO brain homogenates or buffer (B, positive control). Relative quantitation was performed via SRM mass spectrometry. FIG. 6 shows the results, which suggest that A8 is less susceptible to hydrolysis by FAAH than the deuterated synaptamide.

Example 5

This Example also demonstrates analysis of the stability of A8 of the present invention based on susceptibility to FAAH hydrolysis.

Method development: The signal was optimized for each compound by ESI positive or negative ionization mode. A MS2 SIM scan was used to optimize the precursor ion and a product ion analysis was used to identify the best fragment for analysis and to optimize the collision energy.

Analysis: Samples were analyzed by LC/MS/MS using a API 3000 coupled with an Shimadzu HPLC and a CTC PAL chilled autosampler, all controlled by MassHunter software (Agilent), all controlled by Analyst software (ABI). After separation on a C18 reverse phase HPLC column (Agilent, Waters, or equivalent). Mobile phase A was 0.1% AcOH in water. Mobile phase B was 0.1% AcOH in methanol. The flow rate was 0.6 mL/min. The gradient program included a 0.5 min hold at 30% B (the starting conditions), followed by a gradient to 100% B over 2.5 min and a 1 min hold at 100% B. The column was then returned to starting conditions and equilibrated over 1.25 min.

Assay Protocol: Assays were performed at 37° C. at pH=9.0 and involved the use of 0.1 U of FAAH. Reaction was started by adding the substrate amides to sample to reach a final concentration of 1 µM. Reaction was terminated after an appropriate time by using protein precipitation treatment with acetonitrile (3:1, v/v).

Table 3 shows the results of the time course FAAH enzyme assay. The results suggest that A8 is less susceptible to hydrolysis by FAAH than synaptamide or AEA (anandamide).

TABLE 3

| NCGC ID | NCGC00248435 | NCGC00161198 | NCGC00161195 |
|---|---|---|---|
| Other ID | A8 | synaptamide | AEA |
| Conc. | 1 mM | 1 mM | 1 mM |
| Time (min) | % remaining | % remaining | % remaining |
| 0 | 99 | 100 | 74 |
| 30 | 101 | 5 | 1 |
| 60 | 85 | 1 | 1 |

Example 6

This Example provides pharmacokinetic data for A8. Table 4 shows the study design.

TABLE 4

Study Design

| Treatment Group | Treatment | No. of animals | Route of admin. | Dose Level (mg/kg) | Dose Conc. (mg/mL) | Dose Volume (mL/kg) | Time points |
|---|---|---|---|---|---|---|---|
| 1 | NCGC00248435-03 | 33 | IP | 50 | 5 | 10 | Predose, 0.083, 0.25, 0.5, 1, 2, 3, 4, 8, 12 and 24 hr for Plasma and brain collection |

| | |
|---|---|
| Test article | NCGC00248435-03 |
| Test system | C57BL/6 mice, 20-25 g, male, N = 33, purchased from SLAC Laboratory Animal Co. LTD Qualification No.: SCXK (SH) 2007-0005 31283 |
| Food status | Free access to food and water |
| Administration | IP: 50 mg/kg (10 mL/kg) via left quadrant injection (N = 33) |
| Blood collection | The animals were anesthetized with isoflurane and restrained manually at the designated time points. Approximately 120 μL of blood samples were taken from the animals into $K_2$EDTA tube via cardiac puncture. Blood samples were put on ice and centrifuged to obtain plasma sample (2000 g, 5 min under 4° C.) within 15 minutes post sampling. |
| Brain collection | The animal was euthanized by exsanguination. A mid-line incision was made in the animals scalp and skin retracted. The skull overlying the brain was removed. The whole brain was collected, rinsed with cold saline, dried on filtrate paper, weighed and snap frozen by placing into dry-ice. Brain tissue was homogenized for 2 min with 3 volumes (v/w) of homogenizing solution (PBS PH 7.4) right before analysis. |
| Sample storage and disposition | Plasma and brain samples were stored at approximately −80° C. until analysis. |

Table 5 shows the sampling design after IP administration. Each time point is one animal, with 11 time points=33 animals. Each time point was done in triplicate (N=3). The brain and plasma from each animal was analyzed.

TABLE 5

| Dosing route | Time points | Animal No. (#1-#33) |
|---|---|---|
| IP | Pre-dose | #1, #2, #3 |
| | 0.083 | #4, #5, #6 |
| | 0.25 | #7, #8, #9 |
| | 0.5 | #10, #11, #12 |
| | 1 | #13, #14, #15 |
| | 2 | #16, #17, #18 |
| | 3 | #19, #20, #21 |
| | 4 | #22, #23, #24 |
| | 8 | #25, #26, #27 |
| | 12 | #28, #29, #30 |
| | 24 | #31, #32, #33 |

TABLE 5-continued

Table 6 shows formulation preparation information for NCGC00248435-03 for IP dosing.

TABLE 6

| Compound ID | NCGC00248435-03 | Appearance | NA |
|---|---|---|---|
| MW (free base) | 399.61 | FW (salt form) | NA |
| Purity | NA | Color | oil |

NA: not available

Formulation preparation:
IP: 5% DMAC+5% Solutol HS15+90% Saline
50 mg/kg, 10 mL/kg
Weigh 60.97 mg NCGC00248435-03 to a clean vial. Add 0.610 mL of DMAC (Sigma, 18296kk) into the vial. Vortex the tube for 1-2 min and sonicate for 3-4 min. Add 0.610 mL of Solutol HS 15 (BASF, 08333356P0) into the vial. Vortex the tube for 1-2 min and sonicate for 2-3 min. Add 10.975 mL Saline into the tube. Vortex the tube for 2-3 min. The formulation was prepared just prior to use.

Analytical method:
Instrument: LCMSMS-6 (Agilent 6410, triple quadrupole)
Matrix: Mouse plasma and brain homogenate
Analyte(s): NCGC00248435-03
Internal standard(s): Diclofenac
MS conditions: Positive, ESI
MRM detection
NCGC00248435-03: [M+H]+m/z 400.3→72.2
Diclofenac: [M+H]+m/z 296.0→214.0
HPLC conditions for plasma
Mobile phase:
Mobile Phase A: H2O—0.025% FA—1 mM NH4OAc
Mobile Phase B: MeOH—0.025% FA—1 mM NH4OAc

| Time (min) | Pump B (%) |
| --- | --- |
| 0.30 | 30 |
| 0.50 | 98 |
| 2.20 | 98 |
| 2.21 | 30 |
| 3.50 | stop |

Column: Ultimate-XB-C18 (2.1×50 mm, 5 μm)
Flow rate: 0.45 mL/min
Retention time:
NCGC00248435-03: 2.56 min
Diclofenac: 2.14 min
HPLC conditions for brain
Mobile phase:
Mobile Phase A: H2O—0.025% FA—1 mM NH4OAc
Mobile Phase B: ACN—0.025% FA—1 mM NH4OAc

| Time (min) | Pump B (%) |
| --- | --- |
| 0.20 | 20 |
| 0.50 | 98 |
| 2.20 | 98 |
| 2.21 | 20 |
| 3.50 | stop |

Column: Ultimate-XB-C18 (2.1×50 mm, 5 μm)
Flow rate: 0.45 mL/min
Retention time:
  NCGC00248435-03: 2.26 min
  Diclofenac: 2.92 min
Sample preparation:

For plasma samples: An aliquot of 30 μL plasma sample was added with 100 μL ACN (including Diclofenac, 50 ng/mL) for protein precipitation. The mixture was vortexed for 2 min and centrifuged at 12000 rpm for 5 min. The 8 μL supernatant was injected into LC-MS/MS for analysis.

For 10-fold diluted samples: An aliquot of 3 μL plasma sample was added with 27 μL blank plasma to obtain the diluted plasma samples, and the sample dilution factor is 10. The exaction procedure for diluted samples was same as those for non-diluted samples.

For brain samples: Brain sample was homogenized for 2 min with 3 volumes (v/w) of homogenizing solution. An aliquot of 30 μL brain homogenate sample was added with 100 μL ACN (including Diclofenac, 50 ng/mL) for protein precipitation. The mixture was vortexed for 2 min and centrifuged at 12000 rpm for 5 min. The 8 μL supernatant was injected into LC-MS/MS for analysis.

Figure 7:
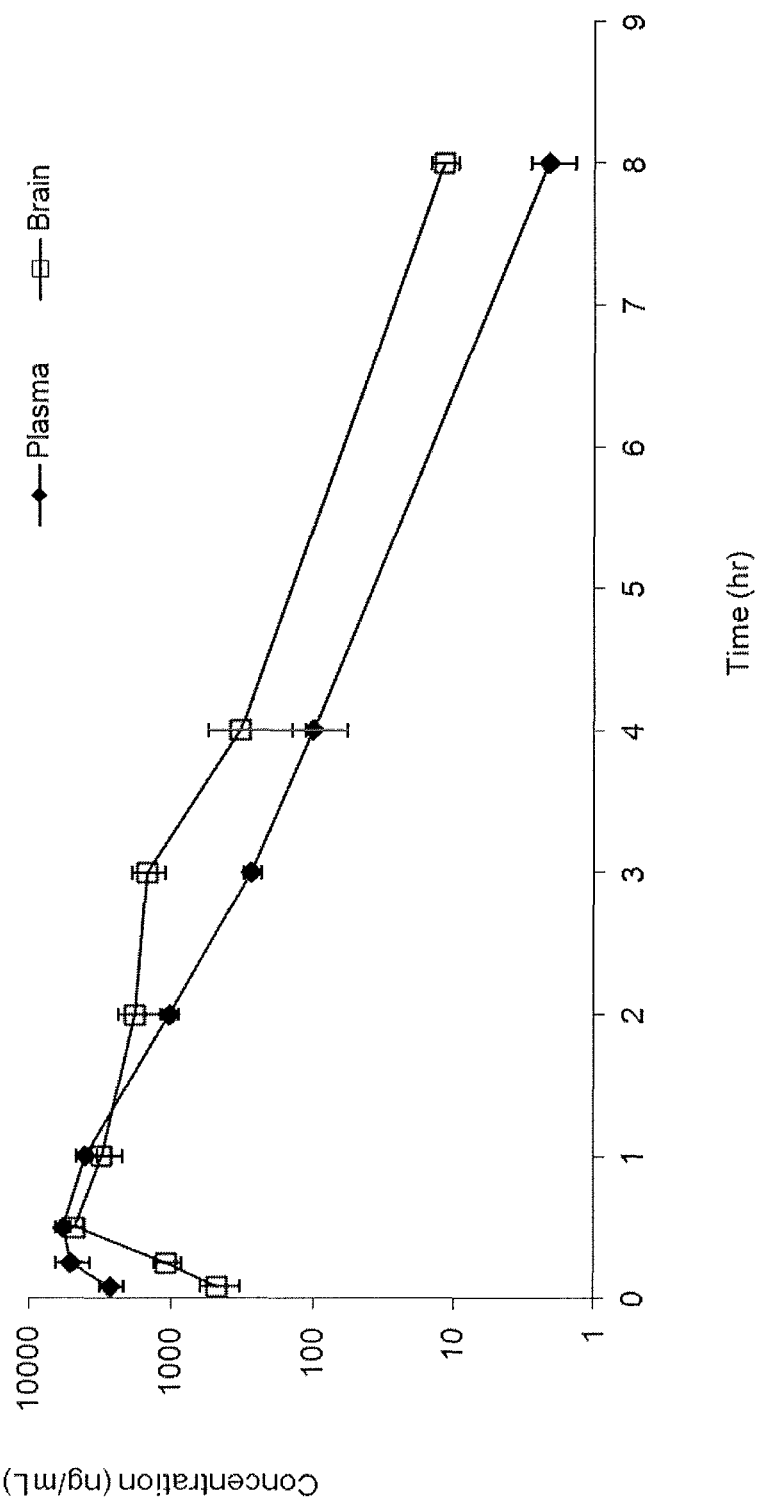
FIG. 7 is a plot presenting pharmacokinetic data generated for A8.

Calibration curve:
  2.00-3000.0 ng/ml for NCGC00248435-03 in C57 mouse plasma
  1.00-3000.0 ng/ml for NCGC00248435-03 in C57 mouse brain homogenate Tables 7 and 8 and FIG. 7 show the results.

TABLE 7

Individual and mean plasma concentration-time data of NCGC00248435-03 after an IP dose of 50 mg/kg in male C57BL/6 mice

| Dose (mg/kg) | Dose route | Sampling time (hr) | Concentration (ng/mL) Individual | | | Mean (ng/mL) | Mean (uM) | Dose Normalized Mean | SD | CV(%) |
| --- | --- | --- | --- | --- | --- | --- | --- | --- | --- | --- |
| 50 | IP | 0 | BQL | BQL | BQL | BQL | BQL | | NA | NA |
| | | 0.083 | 2092 | 3063 | 2707 | 2621 | 6.558 | 0.131 | 492 | 18.8 |
| | | 0.25 | 6549 | 4892 | 3849 | 5097 | 12.754 | 0.255 | 1362 | 26.7 |
| | | 0.5 | 5959 | 6378 | 5036 | 5791 | 14.492 | 0.290 | 687 | 11.9 |
| | | 1 | 4050 | 4574 | 3252 | 3959 | 9.907 | 0.198 | 666 | 16.8 |
| | | 2 | 1129 | 1064 | 870 | 1021 | 2.555 | 0.051 | 135 | 13.2 |
| | | 3 | 321 | 255 | 249 | 275 | 0.688 | 0.014 | 39.9 | 14.5 |
| | | 4 | 78.4 | 148 | 72.9 | 100 | 0.250 | 0.005 | 42.0 | 42.1 |
| | | 8 | 1.83 | 2.94 | 1.55 | 2.11 | 0.005 | 0.000 | 0.736 | 34.9 |
| | | 12 | BQL | BQL | BQL | BQL | BQL | BQL | NA | NA |
| | | 24 | BQL | BQL | BQL | BQL | BQL | BQL | NA | NA |

| PK parameters | Unit | Estimate |
| --- | --- | --- |
| $T_{max}$ | hr | 0.500 |
| $C_{max}$ | ng/mL | 5791 |
| Terminal $t_{1/2}$ | hr | 0.714 |
| $AUC_{last}$ | hr * ng/mL | 8081 |
| $AUC_{INF}$ | hr * ng/mL | 8083 |

TABLE 8

Individual and mean brain concentration-time data of NCGC00248435-03 after an IP dose of 50 mg/kg in male C57BL/6 mice

| Dose (mg/kg) | Dose route | Sampling time (hr) | Concentration (ng/g) Individual | | | Mean (ng/g) | Mean (uM) | Dose Normalized Mean | SD | CV(%) |
|---|---|---|---|---|---|---|---|---|---|---|
| 50 | IP | 0 | BQL | BQL | BQL | BQL | BQL | | NA | NA |
| | | 0.083 | 554 | 310 | 551 | 472 | 1.181 | 0.024 | 140 | 29.6 |
| | | 0.25 | 853 | 1081 | 1330 | 1088 | 2.723 | 0.054 | 239 | 21.9 |
| | | 0.5 | 5113 | 5013 | 3992 | 4706 | 11.777 | 0.236 | 621 | 13.2 |
| | | 1 | 3651 | 2086 | 3367 | 3035 | 7.595 | 0.152 | 834 | 27.5 |
| | | 2 | 1376 | 2463 | 1494 | 1778 | 4.448 | 0.089 | 596 | 33.5 |
| | | 3 | 1931 | 1410 | 1152 | 1497 | 3.747 | 0.075 | 397 | 26.5 |
| | | 4 | 234 | 585 | 179 | 333 | 0.833 | 0.017 | 221 | 66.3 |
| | | 8 | 8.94 | 13.5 | 13.5 | 12.0 | 0.030 | 0.001 | 2.63 | 21.9 |
| | | 12 | BQL | BQL | BQL | BQL | BQL | BQL | NA | NA |
| | | 24 | BQL | BQL | BQL | BQL | BQL | BQL | NA | NA |

| PK parameters | Unit | Estimate |
|---|---|---|
| $T_{max}$ | hr | 0.500 |
| $C_{max}$ | ng/mL | 4706 |
| Terminal $t_{1/2}$ | hr | 0.794 |
| $AUC_{brain}$ ($AUC_{last}$) | hr * ng/mL | 8458 |
| $AUC_{INF}$ | hr * ng/mL | 8471 |
| $AUC_{brain}/AUC_{plasma}$ | % | 105 |

Slight mobility reduction was observed for all animals post dose and lasted for 1 hr. The IP dosing solution was prepared in 5% DMAC+5% SolutolHS15+90% Saline. Brain was homogenized with 3 volumes (v/w) of PBS (pH7.4) and then analyzed with LC-MS/MS. The Brain concentration was corrected with a dilution factor of 4 as following: Brain concentration=Brain homogenate conc.×4, assuming 1 g wet brain equals to 1 mL. BQL=Below quantifiable limit of 1 ng/mL for NCGC00248435-03 in male C57BL/6 plasma and brain homogenate samples. NA=Not available.

Example 7

This Example provides in vivo data for A8 in mice evaluated using the beam walk test.

For the beam walk test, mice were trained to traverse a narrow beam before injury caused by controlled cortical impact (CCI), and the number of hind foot slips after injury was observed over the course of recovery.

Figure 8:
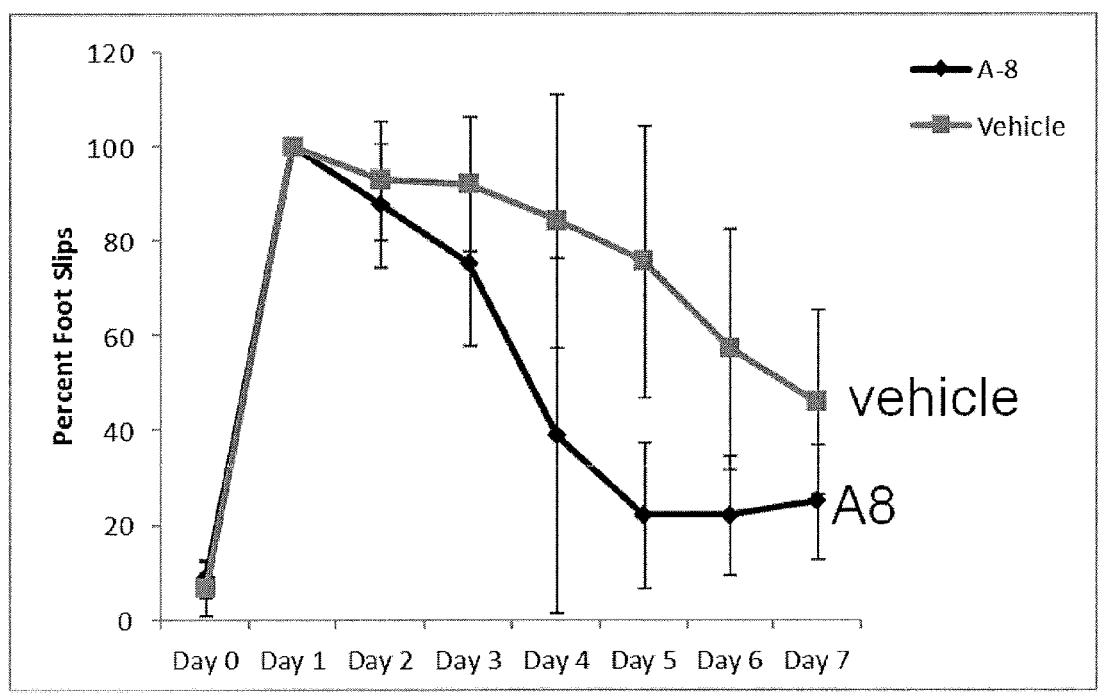
FIG. 8 is a plot presenting in vivo data for A8 in mice evaluated using the beam walk test (FAAH KO mice: n=5 for A8, n=7 for vehicle), in accordance with embodiments of the invention.

A8 has increased resistance to FAAH in comparison to synaptamide but still does show some susceptibility to hydrolysis by FAAH. The effects of A8 in FAAH KO mice were tested by one-time i.p. administration of A8 (25 mg/kg) at 15 min after traumatic brain injury (TBI) inflicted by controlled cortical impact (CCI). The results (FIG. 8) indicated significant improvement of the TBI-induced behavioral deficit from the day 4 after TBI, suggesting therapeutic potential of A8 for functional improvement after TBI.

Example 8

This Example demonstrates analysis of the effect of A8 on neuronal and glial differentiation.

Fetal neural stem cell culture: Neural stem cells (NSCs) were cultured by the neurosphere method (Rietze R. L., Reynolds B. A. (2006) Neural stem cell isolation and characterization. Methods Enzymol. 419, 3-23, the method incorporated by reference herein) with slight modification. Forebrain cortices of rats were isolated on embryonic day 14.5 and 12.5, respectively. The cortices were mechanically disrupted into single cells by repeated pipetting in a serum-free conditioned medium (N2 medium) containing DMEM/F12 (1:1), 0.6% (wt/vol) glucose, 0.1125% (wt/vol) sodium bicarbonate, 2 mM L-glutamine, 5 mM HEPES, 100 μg/mL human apo-transferrin, 20 nM progesterone, 30 nM sodium selenite, 60 μM putrescine, and 25 μg/mL insulin. The dissociated cells were cultured in 6 cm dishes at a density of $1 \times 10^5$ cells/mL in N2 medium with 20 ng/mL bFGF and 2 μg/mL heparin in a humidified 5% $CO_2$/95% air incubator at 37° C. Within 3-4 days, the cells grew as free-floating neurospheres that were then collected by centrifugation, mechanically dissociated by pipetting, and passaged.

Differentiation of NSCs: After the second passage, nestin- and SOX2-positive NSCs were enriched in the neurosphere with minimal presence of differentiated cells (MAP2, Tuj-1 and GFAP-positive cells). After the second passage neurospheres were mechanically dissociated and $5 \times 10^5$ cells/mL were plated onto 15 μg/mL poly-L-ornithine coated 6- or 24-well plates in N2 medium without bFGF and heparin to initiate the differentiation. The cultures were then treated with N2 medium containing A8 in the presence of 40 μM vitamin E for 1-7 days. As the vehicle control, N2 medium containing 40 μM vitamin E was used.

Immunofluorescence staining: For immunofluorescence staining, $2.5 \times 10^5$ NSCs were cultured in 0.5 mL media. Cultured cells were fixed with 4% (wt/vol) paraformaldehyde for 30 min at room temperature, washed with 0.1 M Tris-buffered solution (pH 7.5, TBS), blocked with 10% (vol/vol) normal goat serum in TBS containing 0.3% (vol/vol) Triton X-100 at room temperature for 60 min, and incubated with primary antibodies at 4° C. overnight. The primary antibodies were mouse anti-MAP2 (1:1000) and rabbit anti-glial fibrillary acidic protein (GFAP) (1:2000). The cells were washed with TBS and incubated with Alexa Fluor 488– and 555– conjugated secondary antibodies (1:1000) at room temperature for 60 min. To visualize nuclei, the cells were counterstained with 2 μg/mL 4',6-diamidino-2-phenylindole (DAPI). Finally, the cells were mounted with 80% (vol/vol) glycerol, visualized under a fluorescence microscope and the image data were processed using MetaMorph software for quantitative information. The number of MAP2- and GFAP-positive cells were counted from three separate wells with three to six random fields per well.

Figure 9:
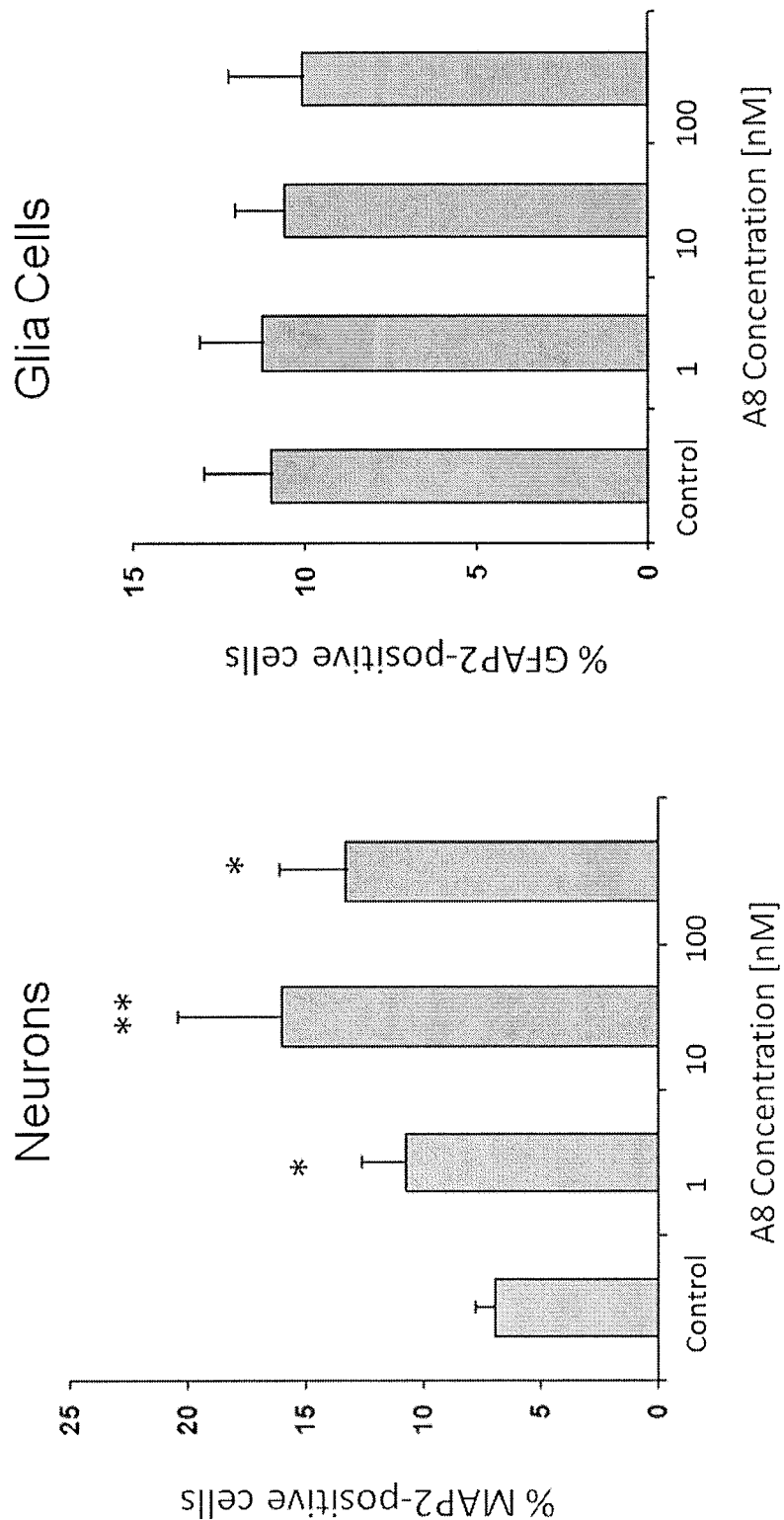
FIG. 9 is a plot presenting expression of MAP2 and GFAP in differentiating neural stem cells treated with A8, in accordance with embodiments of the invention.

NSCs were treated with A8 in the 1-100 nM range for 7 days, and the expression of MAP2 (neuron marker), and GFAP (astrocyte marker) were examined by immunocytochemistry. The immunofluorescence staining data (FIG. 9) showed significant increases in MAP2 positive cells (from 7.0±0.8 to 10.8±1.8%, p=0.02) after treatment with A8 at a concentration as low as 1 nM, while differentiation into GFAP positive cells was not affected, indicating that A8 is a potent neurogenic inducer. The maximum effect of A8 on neuronal differentiation was reached at a concentration around 10 nM (17.2±4.1%, p=0.007).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound having the formula:

$CH_3CH_2HC\!=\!CHCH_2HC\!=\!CHCH_2HC\!=\!CHCH_2HC\!=\!CHCH_2HC\!=\!CHCH_2HC\!=\!CHCH_2CH_2CO\!-\!NR^1R^2$, wherein the group $NR^1R^2$ is selected from:

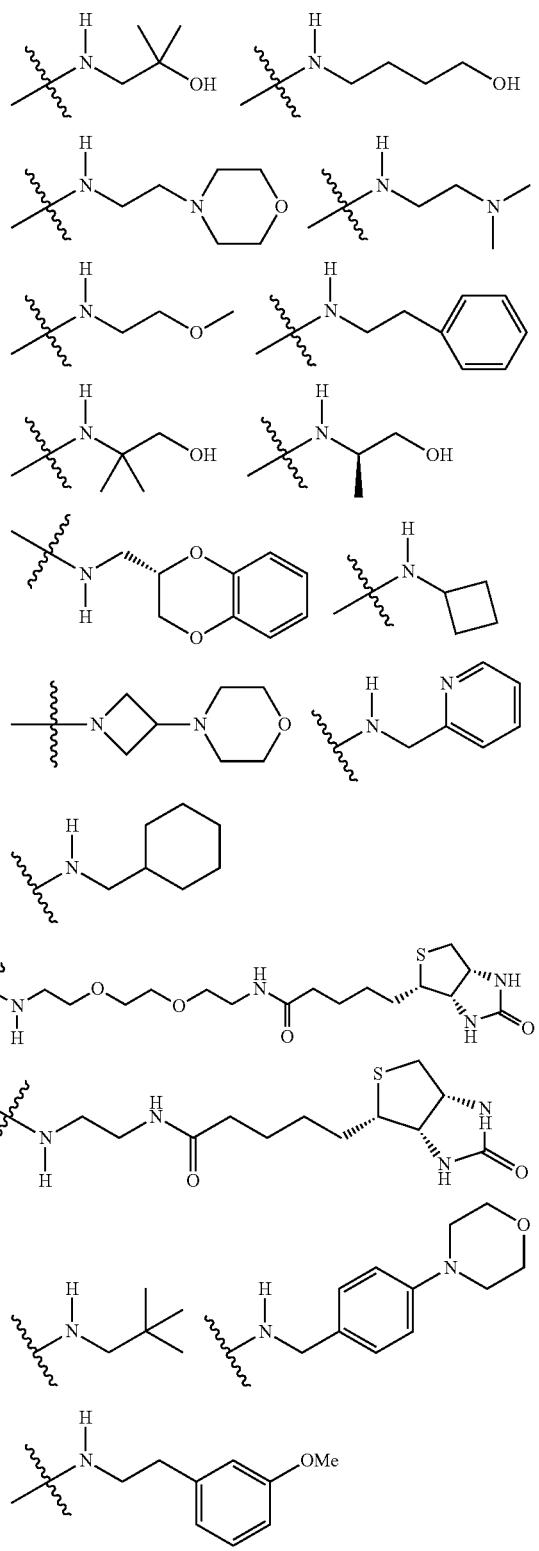

-continued
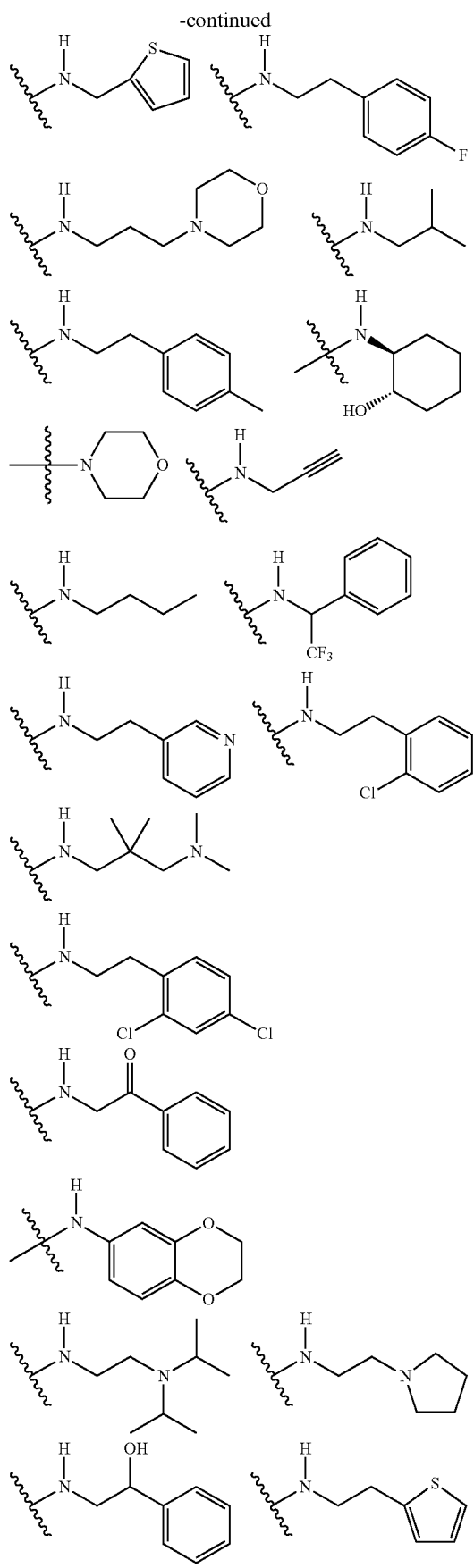
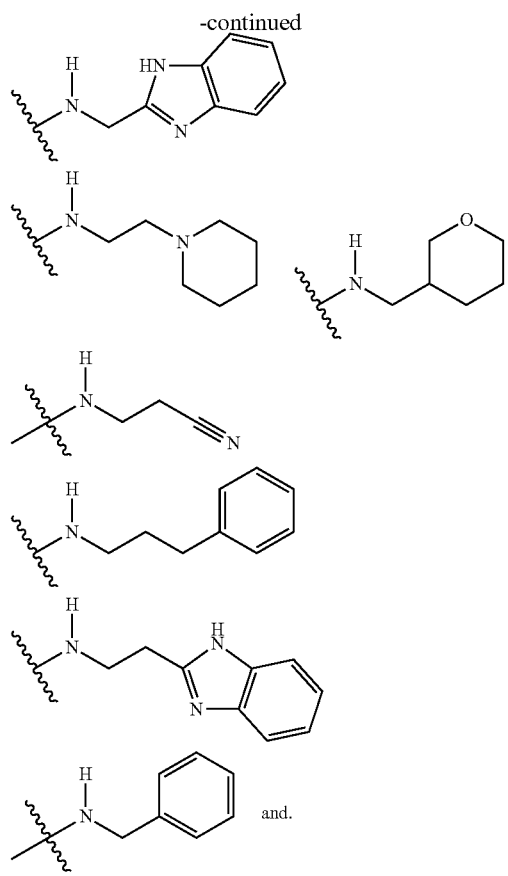
2. The compound of claim 1, wherein the compound is:
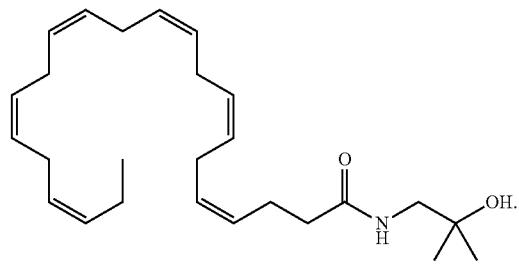
A8
3. The compound of claim 1, wherein the compound is:
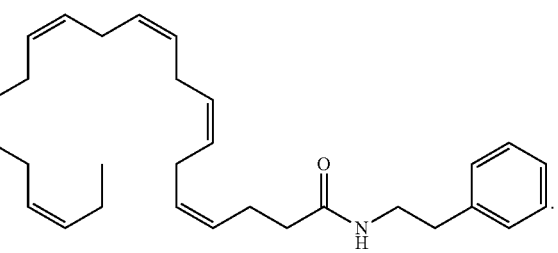
A9

4. The compound of claim 1, wherein the compound is:

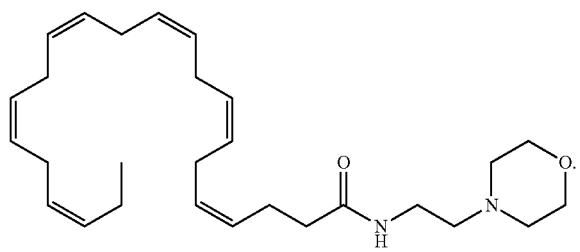
A10

5. The compound of claim 1, wherein the compound is:

CH₃CH₂HC═CHCH₂HC═CHCH₂HC═CHCH₂HC═CHCH₂HC═CHCH₂HC═CHCH₂CH₂CO—NHCH₂CH₂OCH₃.

6. A composition comprising the compound of claim 1 and a pharmaceutically acceptable carrier.

7. A method of increasing neurite growth and/or length within a mammal, the method comprising administering to the mammal an effective amount of a compound, wherein neurite growth and/or length is increased in the mammal, and wherein the compound has the formula:

CH₃CH₂HC═CHCH₂HC═CHCH₂HC═CHCH₂HC═CHCH₂HC═CHCH₂HC═CHCH₂CH₂CO—NR³R², wherein the group NR³R² is selected from:

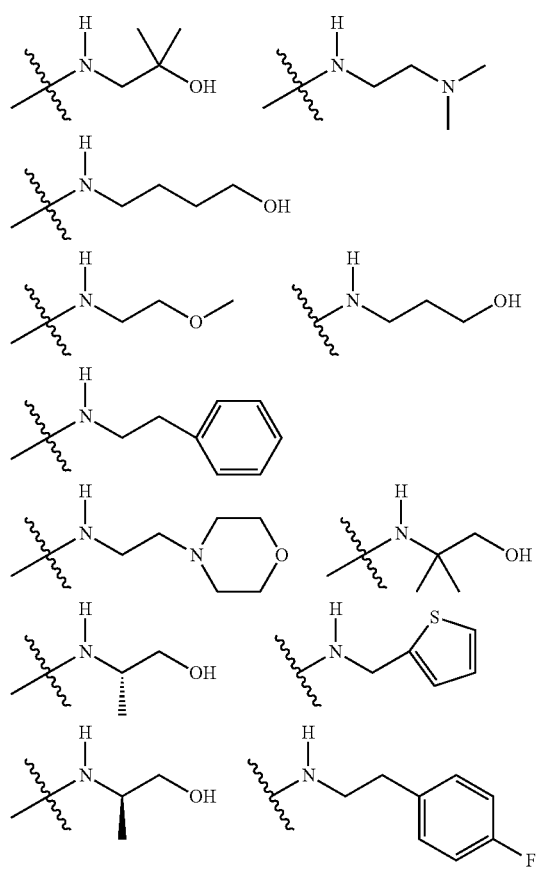

-continued

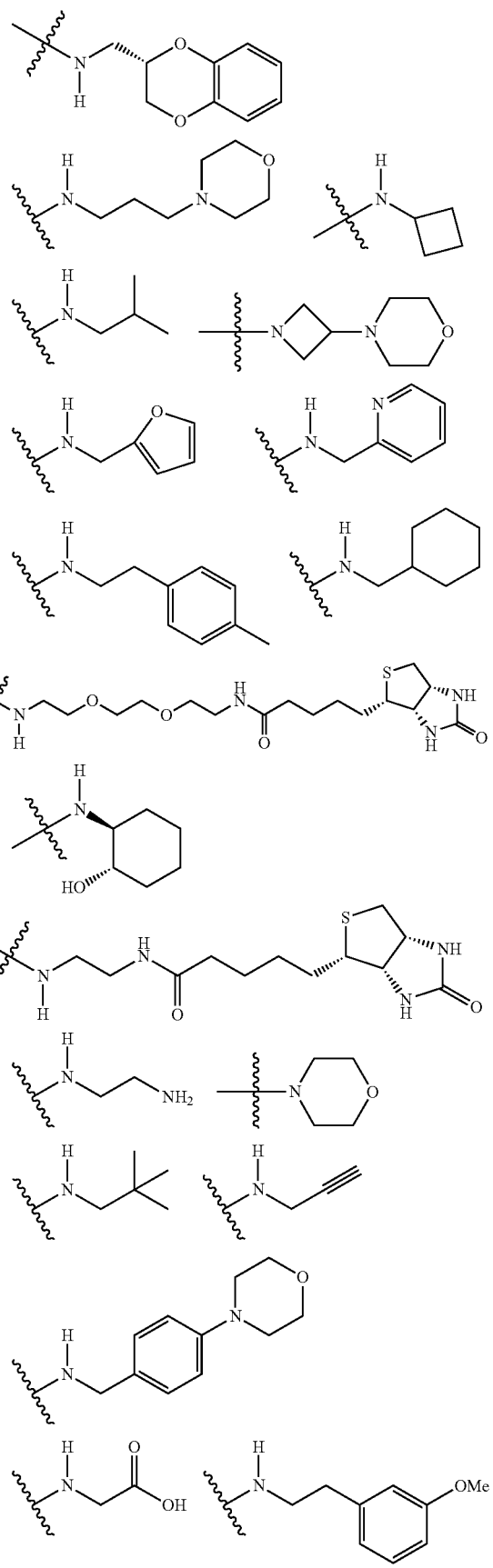

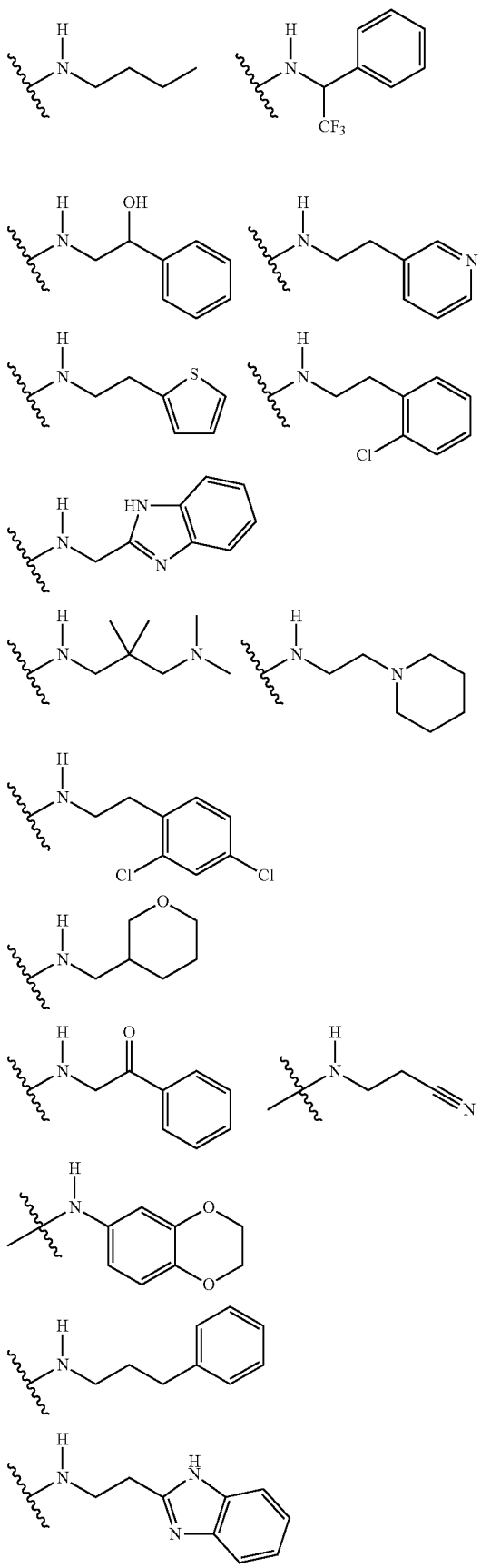

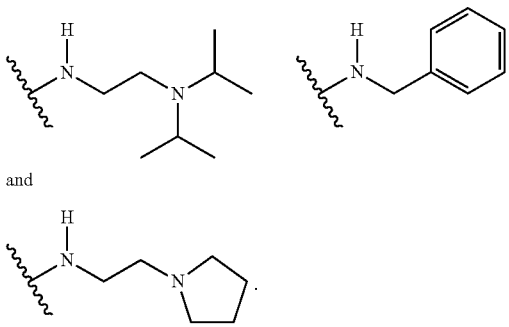

and

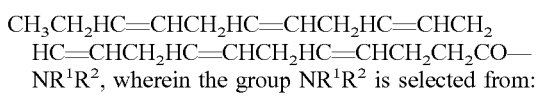

8. The method of claim 7, wherein the mammal has a neurological condition selected from traumatic brain injury, spinal cord injury, peripheral nerve injury, stroke, multiple sclerosis, autism, Alzheimer's disease, Huntington's disease, Parkinson's disease, amyotrophic lateral sclerosis.

9. The method of claim 7, wherein the compound is provided in a pharmaceutically acceptable composition.

10. A method of increasing neurogenesis within a mammal, the method comprising administering to the mammal an effective amount of a compound, wherein neurogenesis is increased in the mammal, and wherein the compound has the formula:

$CH_3CH_2HC=CHCH_2HC=CHCH_2HC=CHCH_2HC=CHCH_2HC=CHCH_2HC=CHCH_2CH_2CO-NR^1R^2$, wherein the group $NR^1R^2$ is selected from:

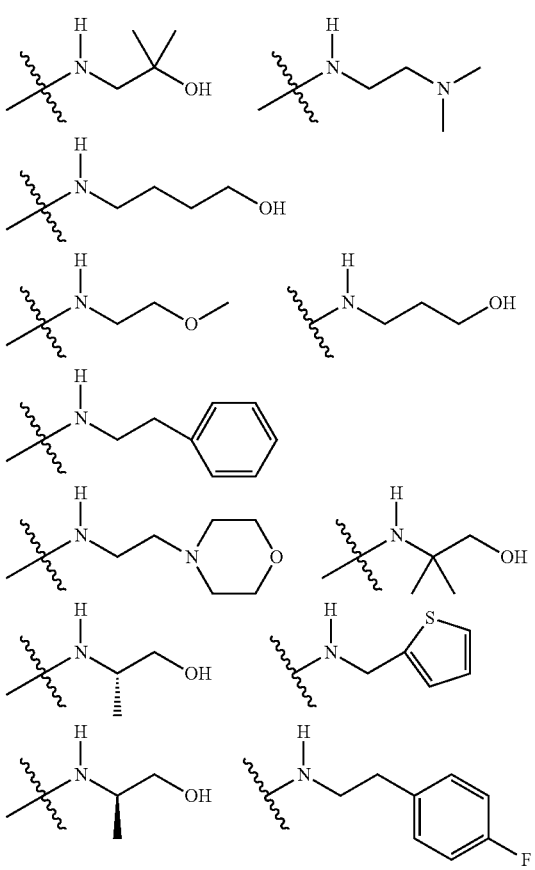

61
-continued
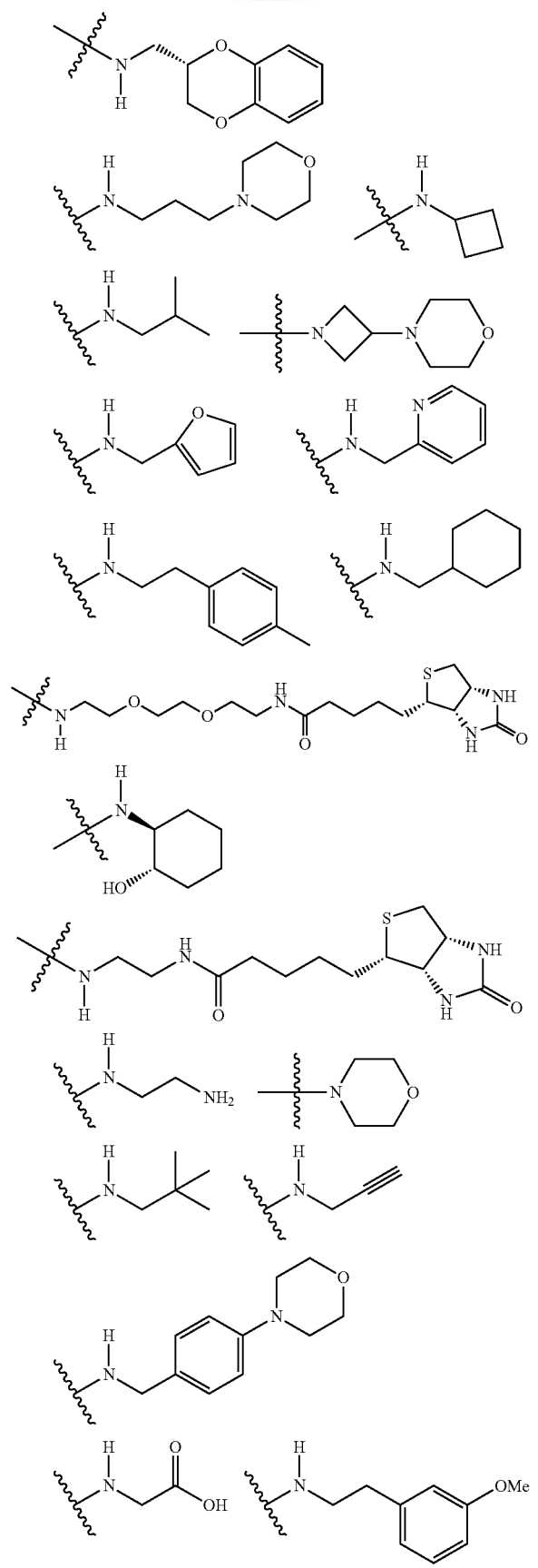
62
-continued
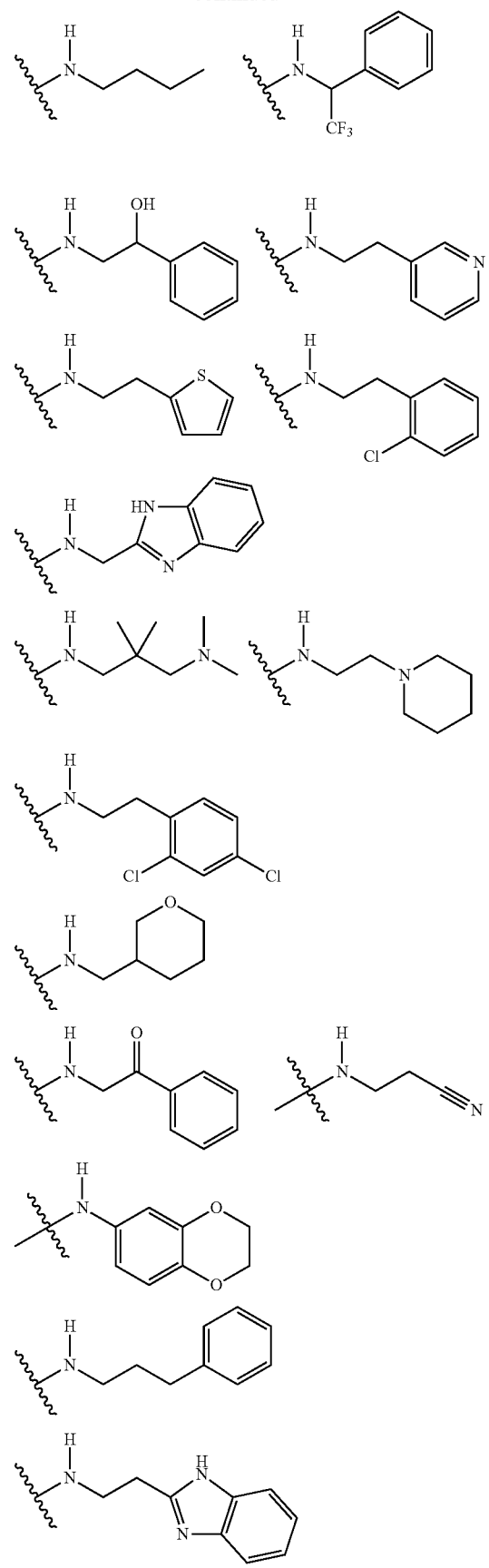

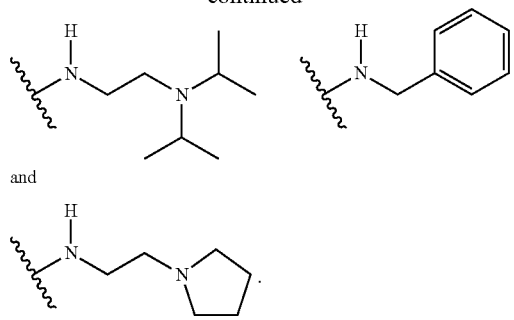

11. The method of claim 10, wherein the mammal has a neurological condition selected from traumatic brain injury, spinal cord injury, peripheral nerve injury, stroke, multiple sclerosis, autism, Alzheimer's disease, Huntington's disease, Parkinson's disease, amyotrophic lateral sclerosis.

12. The method of claim 10, wherein the compound is provided in a pharmaceutically acceptable composition.

13. The method of claim 7, wherein the compound has the formula:
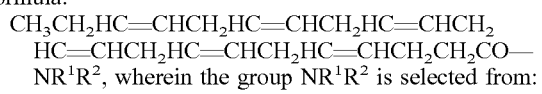
NR$^1$R$^2$, wherein the group NR$^1$R$^2$ is selected from:

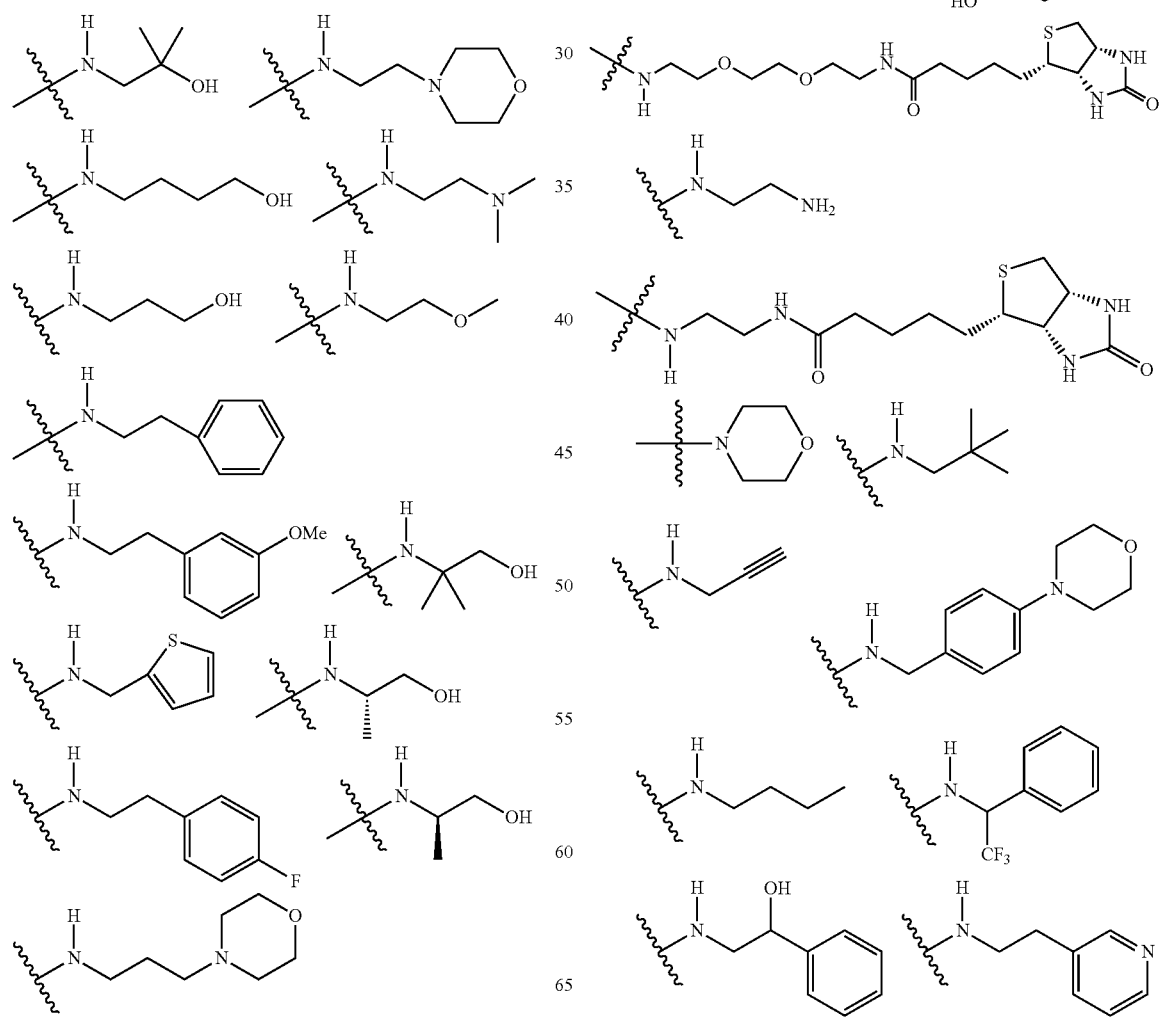

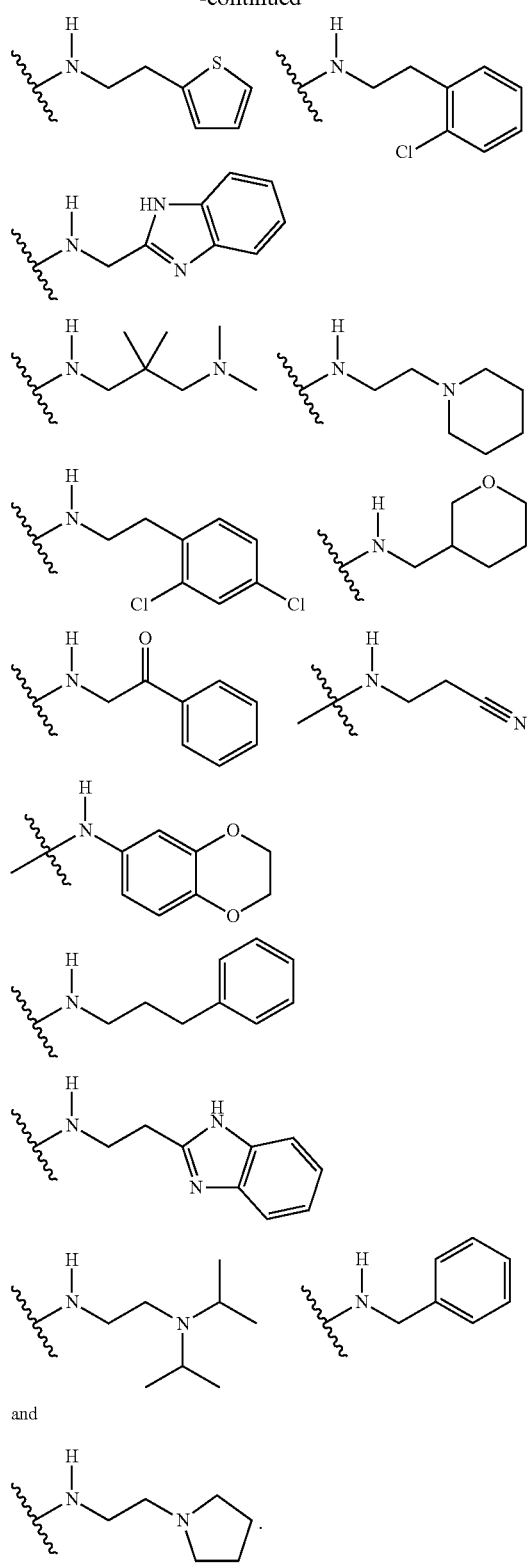
and
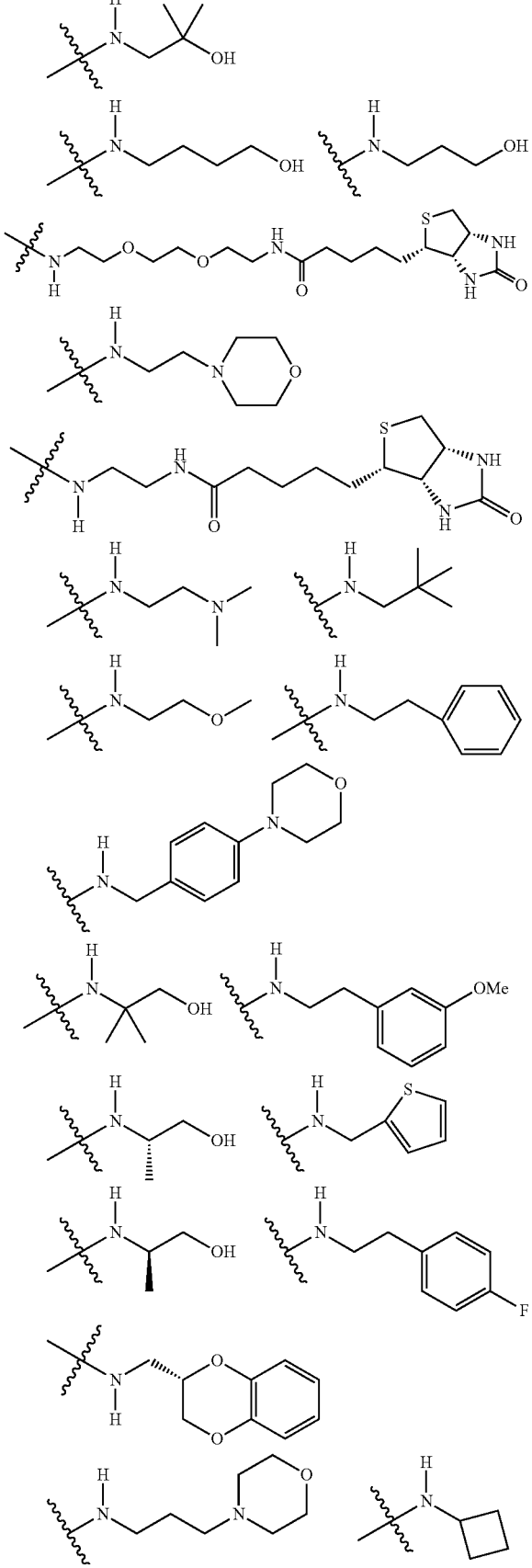
14. The method of claim 10, wherein the compound has the formula:
CH$_3$CH$_2$HC=CHCH$_2$HC=CHCH$_2$HC=CHCH$_2$HC=CHCH$_2$HC=CHCH$_2$HC=CHCH$_2$CH$_2$CO—NR$^1$R$^2$, wherein the group NR$^1$R$^2$ is selected from:

-continued
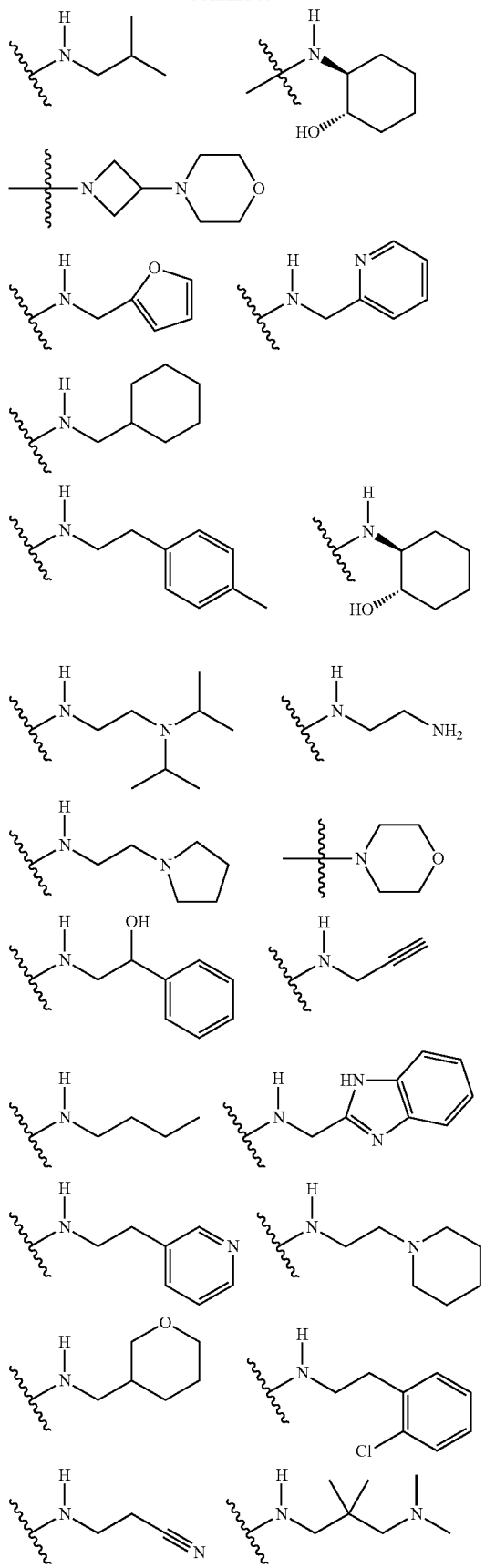
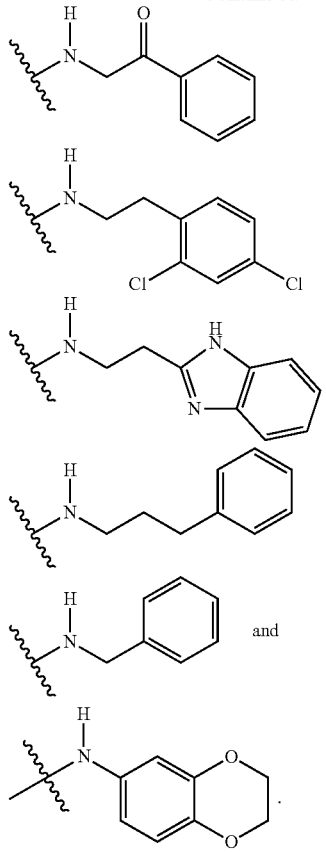
15. The method of claim 7, wherein the compound is:
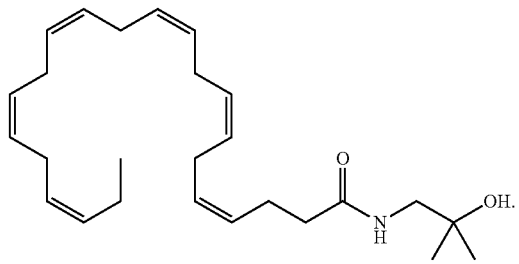
A8
16. The method of claim 7, wherein the compound is:
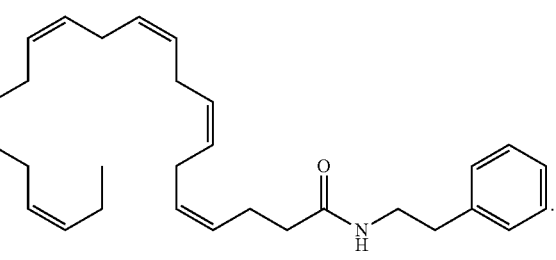
A9

17. The method of claim 7, wherein the compound:

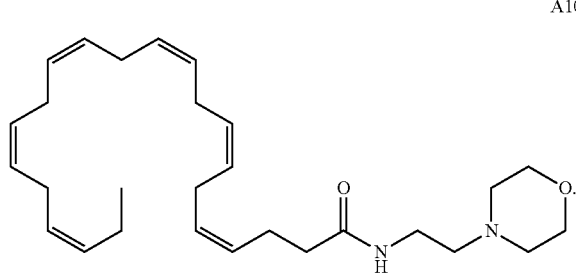 [SMILES: CC/C=C\C/C=C\C/C=C\C/C=C\C/C=C\C/C=C\CCC(=O)NCCc1ccccc1]
A10

18. The method of claim 7, wherein the compound is:
CH₃CH₂HC=CHCH₂HC=CHCH₂HC=CHCH₂HC=CHCH₂HC=CHCH₂HC=CHCH₂CH₂CO—NHCH₂CH₂OCH₃.

19. The method of claim 10, wherein the compound is:

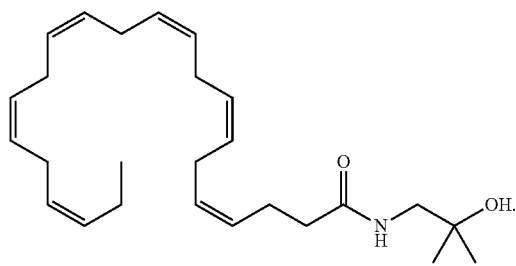
A8

20. The method of claim 10, wherein the compound is:

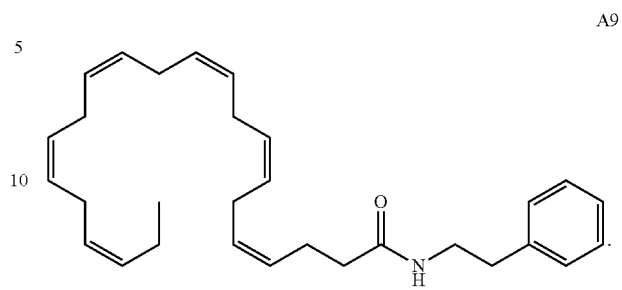
A9

21. The method of claim 10, wherein the compound is:

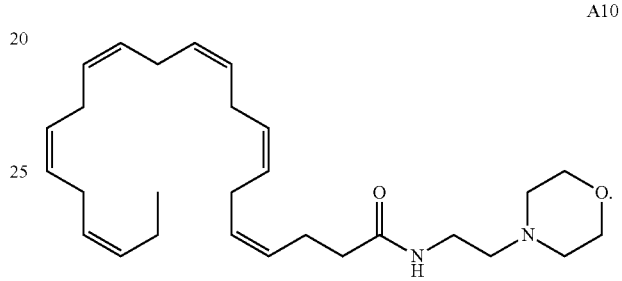
A10

22. The method of claim 10, wherein the compound is:
CH₃CH₂HC=CHCH₂HC=CHCH₂HC=CHCH₂HC=CHCH₂HC=CHCH₂HC=CHCH₂CH₂CO—NHCH₂CH₂OCH₃.

* * * * *